(12) United States Patent
Hibner et al.

(10) Patent No.: US 8,568,333 B2
(45) Date of Patent: Oct. 29, 2013

(54) GRID AND ROTATABLE CUBE GUIDE LOCALIZATION FIXTURE FOR BIOPSY DEVICE

(75) Inventors: John A. Hibner, Mason, OH (US); Kreena Avimukta, Mason, OH (US); Kevin R. Shannon, Mason, OH (US)

(73) Assignee: Devicor Medical Products, Inc., Cincinnati, OH (US)

(*) Notice: Subject to any disclaimer, the term of this patent is extended or adjusted under 35 U.S.C. 154(b) by 1452 days.

(21) Appl. No.: 11/415,467

(22) Filed: May 1, 2006

(65) Prior Publication Data

US 2007/0255168 A1    Nov. 1, 2007

(51) Int. Cl.
*A61B 10/00* (2006.01)
*A61B 19/00* (2006.01)

(52) U.S. Cl.
USPC ............ 600/567; 600/562; 600/564; 606/130

(58) Field of Classification Search
USPC .................................. 600/562, 564; 606/130
See application file for complete search history.

(56) References Cited

U.S. PATENT DOCUMENTS

| | | | |
|---|---|---|---|
| 5,526,822 A | 6/1996 | Burbank et al. | |
| 5,649,547 A | 7/1997 | Ritchart et al. | |
| 5,660,185 A | 8/1997 | Shmulewitz et al. | |
| 5,681,327 A | 10/1997 | Heywang-Koebrunner | |
| 5,702,405 A | 12/1997 | Heywang-Koebrunner | |
| 5,769,086 A | 6/1998 | Ritchart et al. | |
| 5,775,333 A | 7/1998 | Burbank et al. | |
| 5,855,554 A | 1/1999 | Schneider et al. | |
| 5,928,164 A | 7/1999 | Burbank et al. | |
| 5,964,716 A | 10/1999 | Gregoire et al. | |
| 5,980,469 A | 11/1999 | Burbank et al. | |
| 6,007,497 A | 12/1999 | Huitema | |
| 6,017,316 A | 1/2000 | Ritchart et al. | |
| 6,077,230 A | 6/2000 | Gregoire et al. | |

(Continued)

FOREIGN PATENT DOCUMENTS

| | | |
|---|---|---|
| EP | 0640842 | 3/1995 |
| EP | 1815815 | 8/2007 |

(Continued)

OTHER PUBLICATIONS

EPO Search Report for Application. No. 07251817.8, dated Aug. 28, 2007.

(Continued)

*Primary Examiner* — Max Hindenburg
*Assistant Examiner* — Adam Eiseman
(74) *Attorney, Agent, or Firm* — Frost Brown Todd LLC

(57) ABSTRACT

A biopsy system with a grid plate used as either a lateral or medial compression plate of a localization fixture used with a breast coil includes a rotatable guide cube that may be inserted into a desired rectangular recess in the grid plate after rotating to position a selected guide hole in the desired spatial orientation. Versions of a guide cube include those rotatable in two axes to provide additional hole positions, angled holes, enlarged circular holes that function with a rotating guide to support a noncircular biopsy instrument cannula (e.g., trocar/sleeve combination, core biopsy probe of a biopsy device) for rotation. A rotating guide may have an unlocked state for easily sliding to a selected longitudinal position thereon. Thereafter, the rotating guide is locked to serve as a positive depth stop (e.g., quarter turn locking elastomeric rings, triangular and scissor clips, and shutter depth stops).

14 Claims, 23 Drawing Sheets

(56) References Cited

U.S. PATENT DOCUMENTS

| | | |
|---|---|---|
| 6,086,544 A | 7/2000 | Hibner et al. |
| 6,120,462 A | 9/2000 | Hibner et al. |
| 6,228,055 B1 | 5/2001 | Foerster et al. |
| 6,231,522 B1 | 5/2001 | Voegele et al. |
| 6,273,862 B1 | 8/2001 | Privitera et al. |
| 6,743,177 B2 | 6/2004 | Ito |
| 6,752,768 B2 | 6/2004 | Burdorff et al. |
| 6,913,463 B2 * | 7/2005 | Blacklock .................. 433/72 |
| 7,769,426 B2 | 8/2010 | Hibner et al. |
| 7,826,883 B2 | 11/2010 | Hibner et al. |
| 2003/0199753 A1 | 10/2003 | Hibner et al. |
| 2005/0080333 A1 | 4/2005 | Piron et al. |
| 2005/0283069 A1 | 12/2005 | Hughes et al. |
| 2007/0135821 A1 * | 6/2007 | Shabaz .................. 606/130 |
| 2007/0233157 A1 | 10/2007 | Mark et al. |

FOREIGN PATENT DOCUMENTS

| | | |
|---|---|---|
| GB | 2 105 997 | 4/1983 |
| WO | WO 01/02073 | 1/2001 |
| WO | WO 02/13709 | 2/2002 |
| WO | WO 2007/070285 | 6/2007 |

OTHER PUBLICATIONS

Japanese Office Action dated Apr. 10, 2012 for Application No. JP 2007-119013.

Communication dated Jul. 6, 2011 from Application No. EP 07 251 817.8.

* cited by examiner

GRID AND ROTATABLE CUBE GUIDE LOCALIZATION FIXTURE FOR BIOPSY DEVICE

CROSS REFERENCE TO RELATED APPLICATIONS

The present application is related to the co-pending and commonly-owned U.S. patent application Ser. No. 11/414,988, "BIOPSY CANNULA ADJUSTABLE DEPTH STOP" to Hibner et al., filed on even date herewith, the disclosure of which is hereby incorporated by reference in its entirety.

FIELD OF THE INVENTION

The present invention relates in general to biopsy devices, and more particularly to biopsy devices having a cutter for severing tissue, and even more particularly to a localization and guidance fixture that guides insertion of a probe, or a sleeve that subsequently receives the probe of a biopsy device.

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has an advantage in that it is very low-pain, so low-pain that local anesthetic is not always used because the application of it may be more painful than the FNA itself. However, a shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed allowing for a pathological assessment of the tissue, including an assessment of the progression of any cancerous cells that are found. The following patent documents disclose various core biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and U.S. Patent Application 2003/0199753 published Oct. 23, 2003 to Hibner et al.

In U.S. Pat. Appln. Publ. No. 2005/0283069A1, "MRI biopsy device localization fixture" to Hughes et al., the disclosure of which is hereby incorporated by reference in its entirety, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a sleeve to a biopsy site of suspicious tissues or lesions. A z-stop enhances accurate insertion, and prevents over-insertion or inadvertent retraction of the sleeve.

While this three-axes localization fixture has a large number of advantages, including supporting a handle of the biopsy device during hands off portions of the procedure, some clinicians prefer, or are at least more familiar with, other approaches to guiding a probe of a biopsy device. For instance, an EnCor™ Needle Guide Block by SenoRx® of Aliso Viejo, Calif., which has a plurality of needle holes between a front and a back face, is inserted into a grid localization fence for guiding an EnCor™ cannula that in turn guides a trocar, obturator or probe of a biopsy device. The guide block may rotate about the longitudinal axis of the block to present more options for an insertion point into breast tissue. A polymeric ring is inserted over the cannula to give a visual indication to the clinician as to the depth of insertion of the cannula/trocar. A perceived benefit of this approach is an intuitive guidance mechanism with relatively inexpensive disposable components.

While these guidance options have clinical effectiveness, a significant desire remains for additional refinements that accurately guide a probe for taking a core biopsy sample.

SUMMARY OF THE INVENTION

The present invention addresses these and other problems of the prior art by providing an apparatus for locating a breast of a patient and guiding a biopsy instrument cannula for insertion into tissue, wherein one of two compression surfaces that are positioned relative to a patient support surface to opposingly compress the patient's breast, is a grid plate having a plurality of grid apertures. The orientation of guide holes formed in the guide cube enhance options for positioning the guide cube to closely position an insertion point.

In one aspect of the invention, a guide device, with guide holes passing transversely to one another between differing pairs of opposing faces, is inserted into a selected one of the guide apertures. A grounding structure between the guide device and the grid plate prevents the guide cube from passing out of a distal side of the grid plate presented against the patient. Thereby, an intuitive approach to guiding a biopsy instrument by placing a guide cube is enhanced by providing multiple faces of the device that may contain centered or off center guide holes. Placing a pair of closely positioned guide holes on the same face may otherwise not effectively guide the biopsy instrument with too much hole overlap. Portions of the biopsy instrument that are not in contact with the guide hole increase force in other areas that may lead to bending or fracture.

In another aspect of the invention, a guide device sized for insertion into the grid plate has guide holes that pass nonorthogonally between proximal and distal faces of the guide device. Thereby, an angle of insertion may be selected that is not merely orthogonal to the grid plate.

In yet another aspect of the invention, an intermediary device of a rotating guide is received over a biopsy instrument, which in turn is received into an enlarged guide hole in a guide cube inserted into the grid plate. The rotating guide thus may serve purposes such as presenting a circular transverse cross section to allow rotation of a nonround biopsy instrument cannula. To give a number of hole positions within a selected grid aperture, a set of guide cubes are presented as a set, each with various unique positions of one or more guide holes. Selecting a guide cube thus gives enhanced flexibility in positioning the insertion point.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Figure 1:
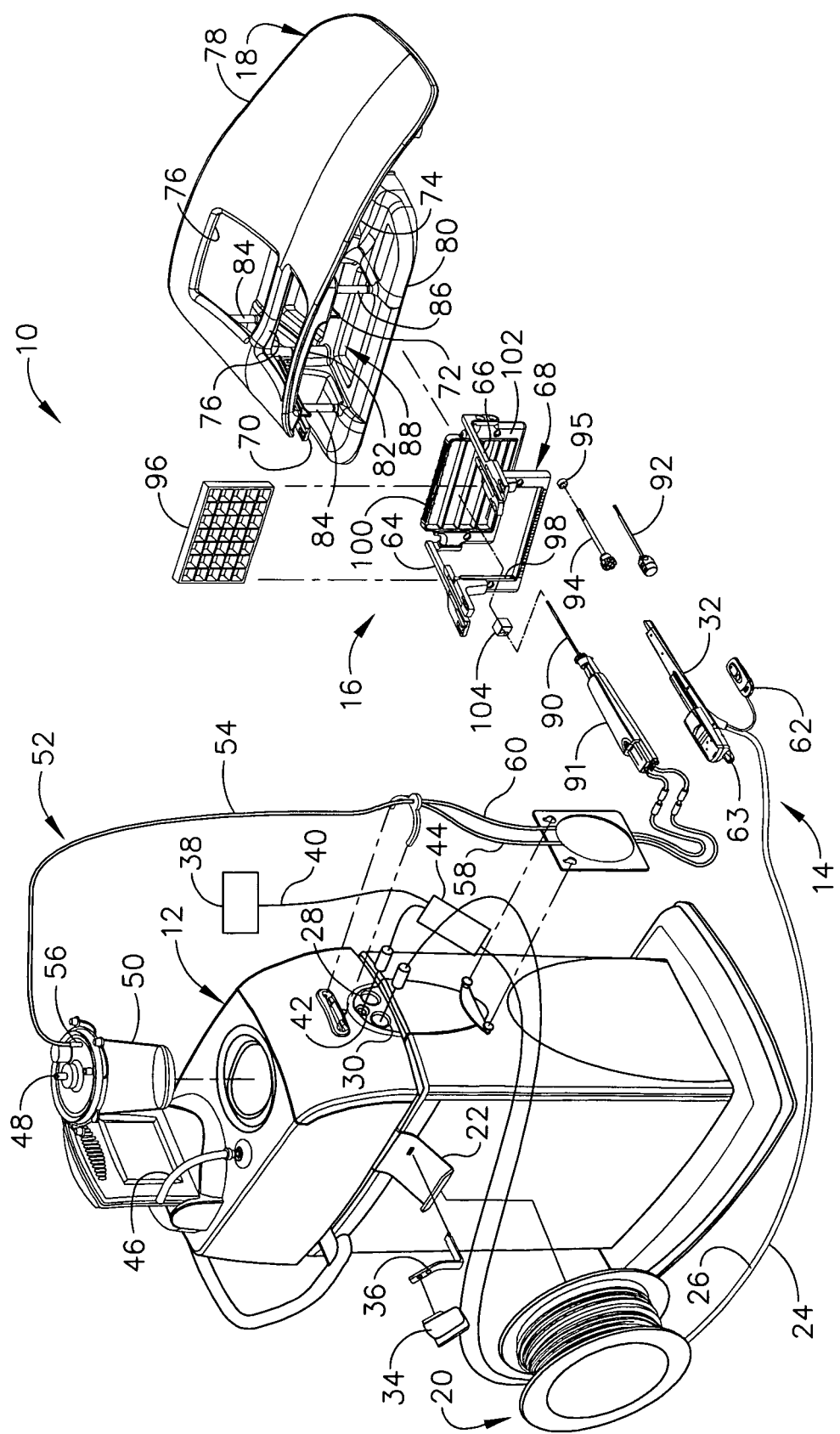
FIG. 1 is an isometric view of a biopsy system including a control module remotely coupled to a biopsy device, and including a localization fixture with a lateral grid plate used in conjunction with a rotatable cube to position a trocar/obturator or a probe of the biopsy device to a desired insertion depth as set by a ring stop.
Figure 2:
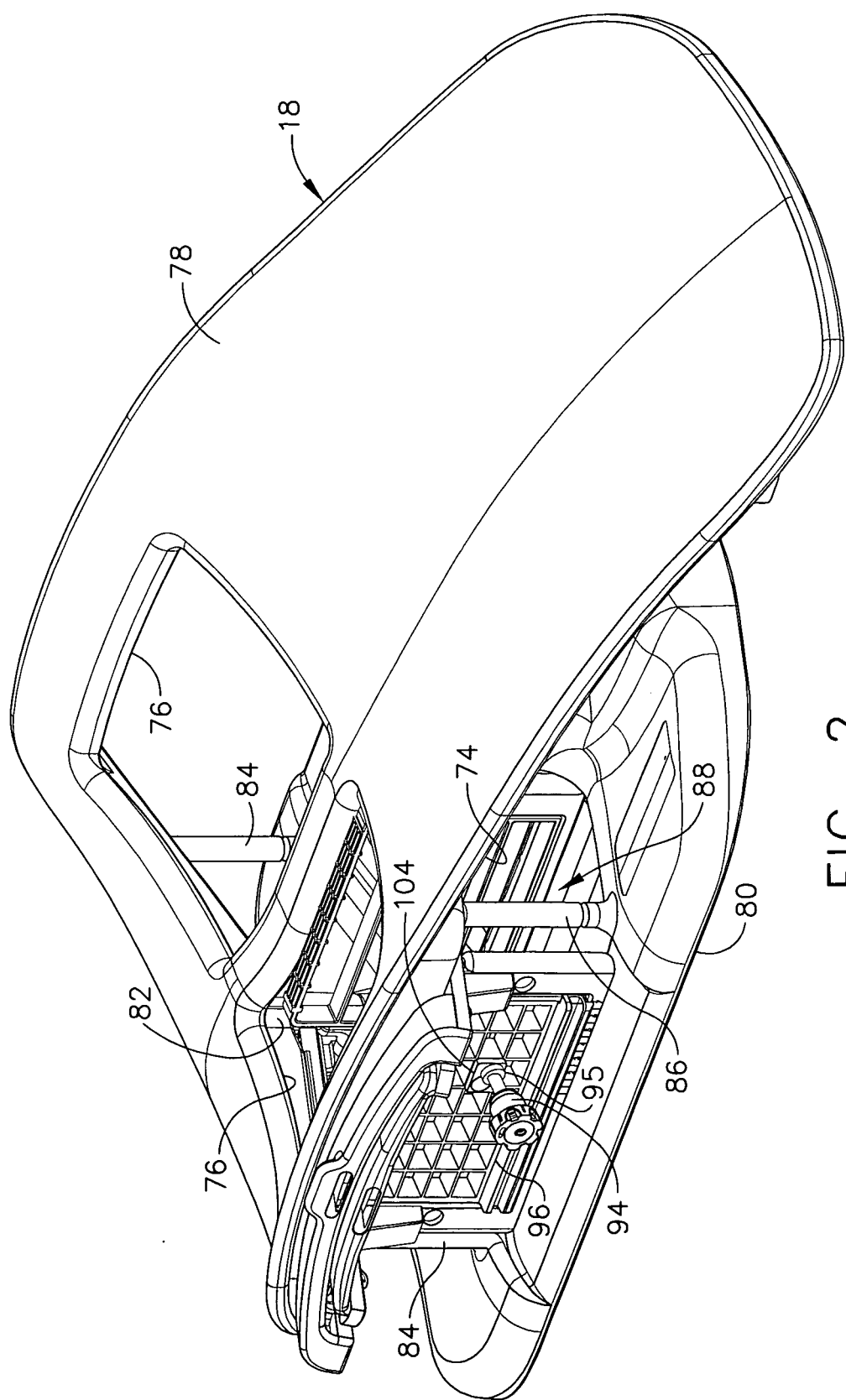
FIG. 2 is an isometric view of the breast coil receiving the localization fixture of FIG. 1.
Figure 3:
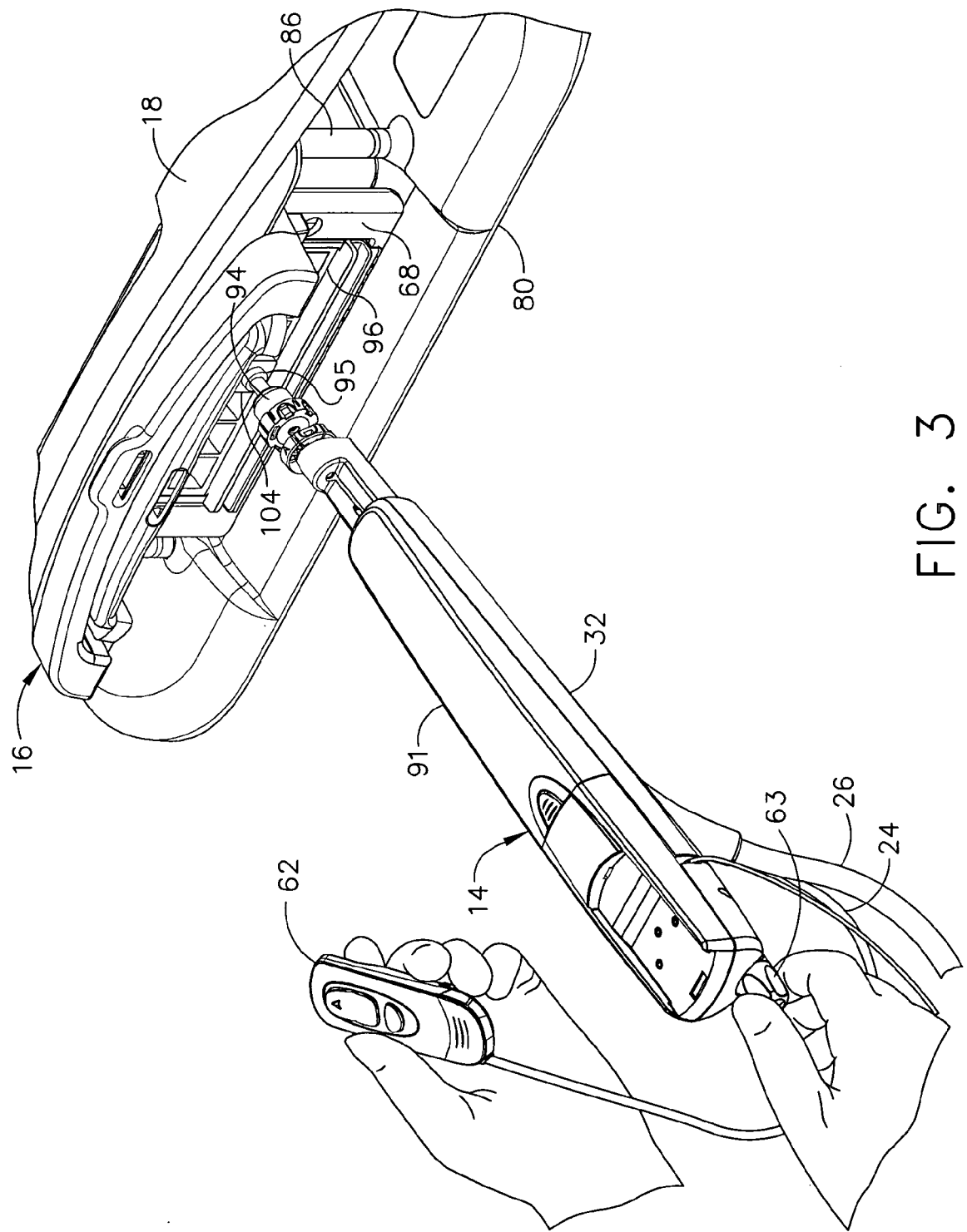
FIG. 3 is an isometric view of the biopsy device inserted through the rotatable cube within the cube plate of the localization fixture attached to a breast coil of FIG. 1.

Turning to the Drawings, wherein like numerals denote like components throughout the several views, in FIGS. 1-3, a Magnetic Resonance Imaging (MRI) compatible biopsy system 10 has a control module 12 that typically is placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality is incorporated into the control module 12 to assist in taking these tissue samples. The control module 12 controls and powers an MRI biopsy device 14 that is positioned and guided by a localization fixture 16 attached to a breast coil 18 that is placed upon a gantry (not shown) of the MRI machine.

The control module 12 is mechanically, electrically, and pneumatically coupled to the MRI biopsy device 14 so that components may be segregated that need to be spaced away from the strong magnetic field and the sensitive RF receiving components of the MRI machine. A cable management spool 20 is placed upon a cable management attachment saddle 22 that projects from a side of the control module 12. Wound upon the cable management spool 20 is a paired electrical cable 24 and mechanical cable 26 for communicating control signals and cutter rotation/advancement motions respectively. In particular, electrical and mechanical cables 24, 26 each have one end connected to respective electrical and mechanical ports 28, 30 in the control module 12 and another end connected to a reusable holster portion 32 of the MRI biopsy device 14. An MRI docking cup 34, which may hold the holster portion 32 when not in use, is hooked to the control module 12 by a docking station mounting bracket 36.

An interface lock box 38 mounted to a wall provides a tether 40 to a lockout port 42 on the control module 12. The tether 40 is advantageously uniquely terminated and of short length to preclude inadvertent positioning of the control module 12 too close to the MRI machine. An in-line enclosure 44 may advantageously register the tether 40, electrical cable 24 and mechanical cable 26 to their respective ports 42, 28, 30 on the control module 12.

Vacuum assist is provided by a first vacuum line 46 that connects between the control module 12 and an outlet port 48 of a vacuum canister 50 that catches liquid and solid debris. A tubing kit 52 completes the pneumatic communication between the control module 12 and the MRI biopsy device 14. In particular, a second vacuum line 54 is connected to an inlet port 56 of the vacuum canister 50. The second vacuum line 54 divides into two vacuum lines 58, 60 that are attached to the MRI biopsy device 14. With the MRI biopsy device 14 installed in the holster portion 32, the control module 12 performs a functional check. Saline is manually injected into biopsy device 14 to serve as a lubricant and to assist in achieving a vacuum seal. The control module 12 actuates a cutter mechanism (not shown) in the MRI biopsy device 14, monitoring full travel. Binding in the mechanical cable 26 or within the biopsy device 14 is monitored with reference to motor force exerted to turn the mechanical cable 26 and/or an amount of twist in the mechanical cable 26 sensed in comparing rotary speed or position at each end of the mechanical cable 26.

A remote keypad 62, which is detachable from the reusable holster portion 32, communicates via the electrical cable 24 to the control panel 12 to enhance clinician control of the MRI biopsy device 14, especially when controls that would otherwise be on the MRI biopsy device 14 itself are not readily accessible after insertion into the localization fixture 16 and/or placement of the control module 12 is inconveniently remote (e.g., 30 feet away). An aft end thumbwheel 63 on the reusable holster portion 32 is also readily accessible after insertion to rotate the side from which a tissue sample is to be taken.

Left and right parallel upper guides 64, 66 of a localization framework 68 are laterally adjustably received respectively within left and right parallel upper tracks 70, 72 attached to an under side 74 and to each side of a selected breast aperture 76 formed in a patient support platform 78 of the breast coil 18. A base 80 of the breast coil 18 is connected by centerline pillars 82 that are attached to the patient support platform 78 between the breast apertures 76. Also, a pair of outer vertical support pillars 84, 86 on each side spaced about a respective breast aperture 76 respectively define a lateral recess 88 within which the localization fixture 16 resides.

It should be appreciated that the patient's breasts hang pendulously respectively into the breast apertures 76 within the lateral recesses 88. For convenience, herein a convention is used for locating a suspicious lesion by Cartesian coordinates within breast tissue referenced to the localization fixture 16 and to thereafter selectively position an instrument, such as a probe 90 (FIG. 1) of a disposable probe assembly 91 that is engaged to the reusable holster portion 32 to form the MRI biopsy device 14. To enhance hands off use of the biopsy system 10, especially for repeated reimaging within the narrow confines of a closed bore MRI machine, the MRI compatible biopsy system 10 may also guide a trocar ("introducer") 92 encompassed by a sleeve 94. Depth of insertion is controlled by a depth stop device 95 longitudinally positioned on either the probe 90 or the sleeve 94.

This guidance is specifically provided by a lateral fence, depicted as a grid plate 96, which is received within a laterally adjustable outer three sided plate bracket 98 attached below the left and right parallel upper guides 64, 66. Similarly, a medial fence with respect to a medial plane of the chest of the patient, depicted as a medial plate 100, is received within an inner three-sided plate bracket 102 attached below the left and right parallel upper guides 64, 66 close to the centerline pillars 82 when installed in the breast coil 18. To further refine the insertion point of the instrument (e.g., probe 90, trocar/sleeve 92, 94), a guide cube 104 is inserted into the backside of the grid plate 96.

The selected breast is compressed along an inner (medial) side by the medial plate 100 and on an outside (lateral) side of the breast by the grid plate 96, the latter defining an X-Y plane. The X-axis is vertical (sagittal) with respect to a standing patient and corresponds to a left-to-right axis as viewed by a clinician facing the externally exposed portion of the localization fixture 16. Perpendicular to this X-Y plane extending toward the medial side of the breast is the Z-axis, which typically corresponds to the orientation and depth of insertion of the probe 90 of the MRI biopsy device 14 or the trocar/sleeve 92, 94. For clarity, the term Z-axis may be used interchangeably with "axis of penetration", although the latter may or may not be orthogonal to the spatial coordinates used to locate an insertion point on the patient. Versions of the localization fixture 16 described herein allow a nonorthogonal axis of penetration to the X-Y axis to a lesion at a convenient or clinically beneficial angle.

Figure 4:
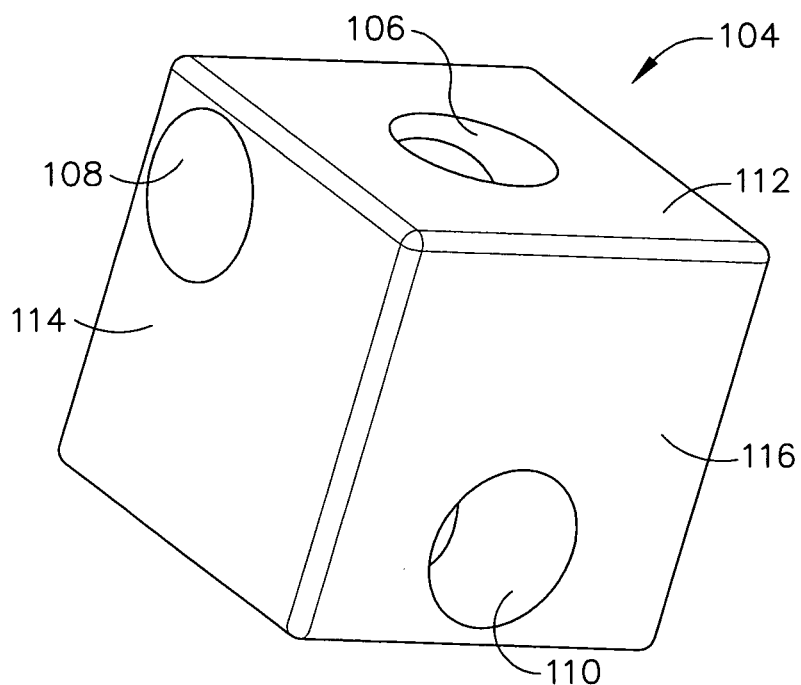
FIG. 4 is an isometric view of a two-axis rotatable guide cube of the biopsy system of FIG. 1.
Figure 5:
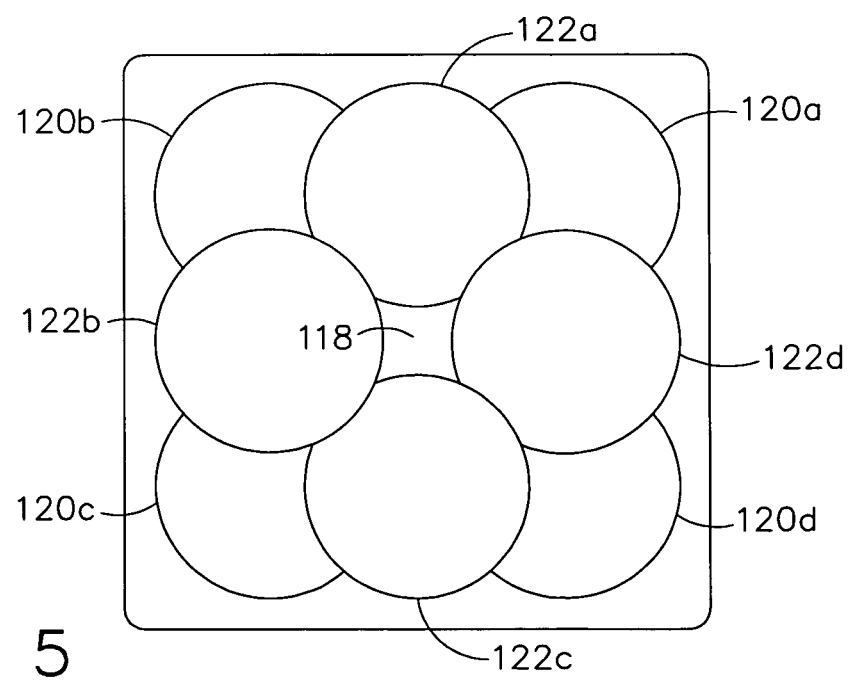
FIG. 5 is a diagram of nine guide positions achievable by the two-axis rotatable guide cube of FIG. 5.

In FIG. 4, guide cube 104 includes a central guide hole 106, a corner guide hole 108, and an off-center guide hole 110 that pass orthogonally to one another between respective opposite pairs of faces 112, 114, 116. By selectively rotating the guide cube 104 in two axis, one of the pairs of faces 112, 114, 116 may be proximally aligned to an unturned position and then the selected proximal face 112, 114, 116 optionally rotated a quarter turn, half turn, or three quarter turn. Thereby, one of nine guide positions 118 (i.e., using central guide hole 106), 120a-120d (i.e., corner guide hole 108), 122a-122d (i.e., using off-center guide hole 110) may be proximally exposed as depicted in FIG. 5.

Figure 6:
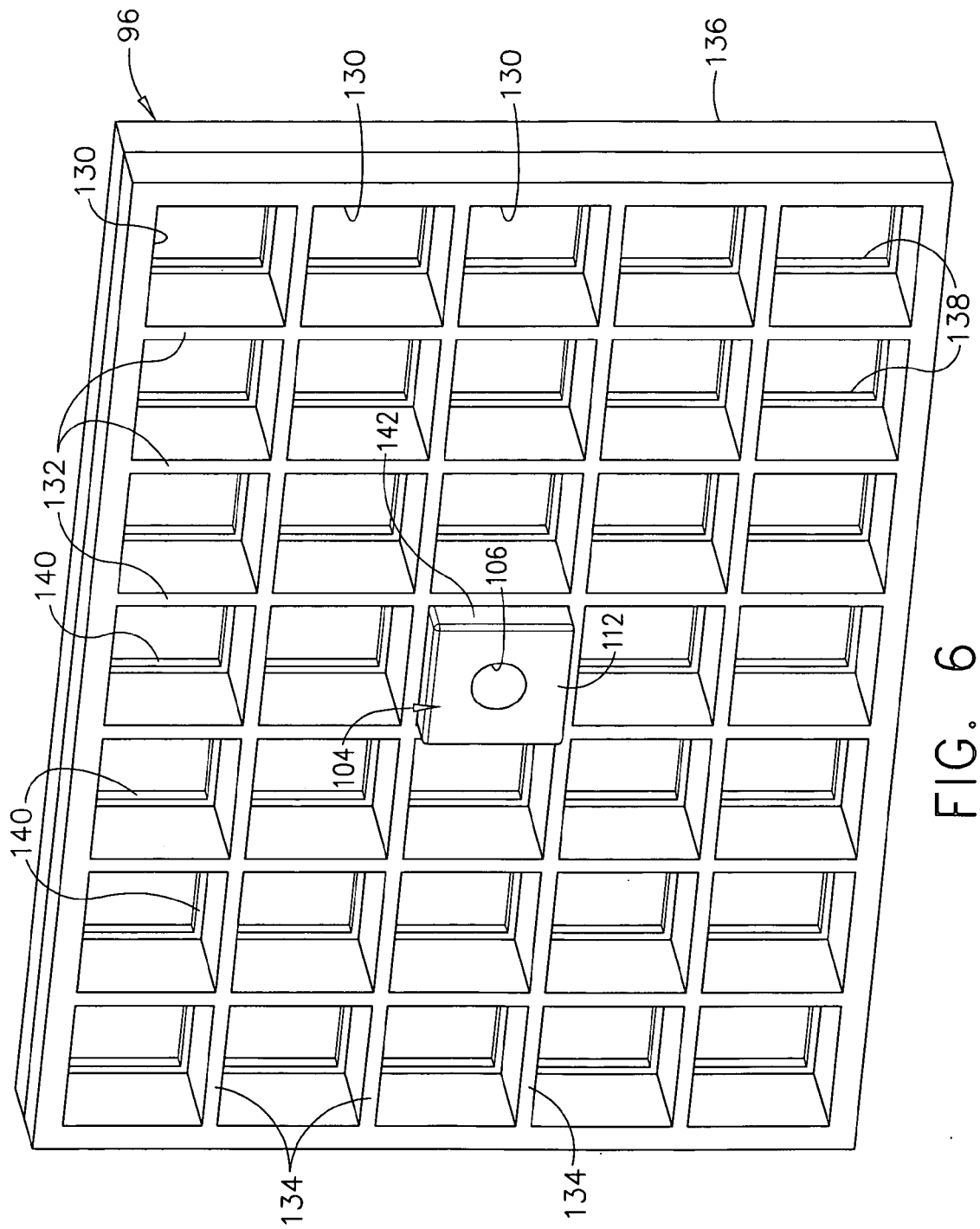
FIG. 6 is an isometric view of a two-axis rotatable guide cube inserted into a lateral grid with the backing of the localization fixture of FIG. 1.

In FIG. 6, the two-axis rotatable guide cube 104 is sized for insertion from a proximal side into one of a plurality of square recesses 130 in the grid plate 96 formed by intersecting vertical bars 132 and horizontal bars 134. The guide cube 104 is prevented from passing through the grid plate 96 by a backing substrate 136 attached to a front face of the grid plate 96. The backing substrate 136 includes a respective square opening 138 centered within each square recess 130, forming a lip 140 sufficient to capture the front face of the guide cube 104 but not so large as to obstruct the guide holes 104, 106, 108. The depth of the square recesses 130 is less than the guide cube 104, thereby exposing a proximal portion 142 of the guide cube 104 for seizing and extraction from the grid plate 96.

Figure 7:
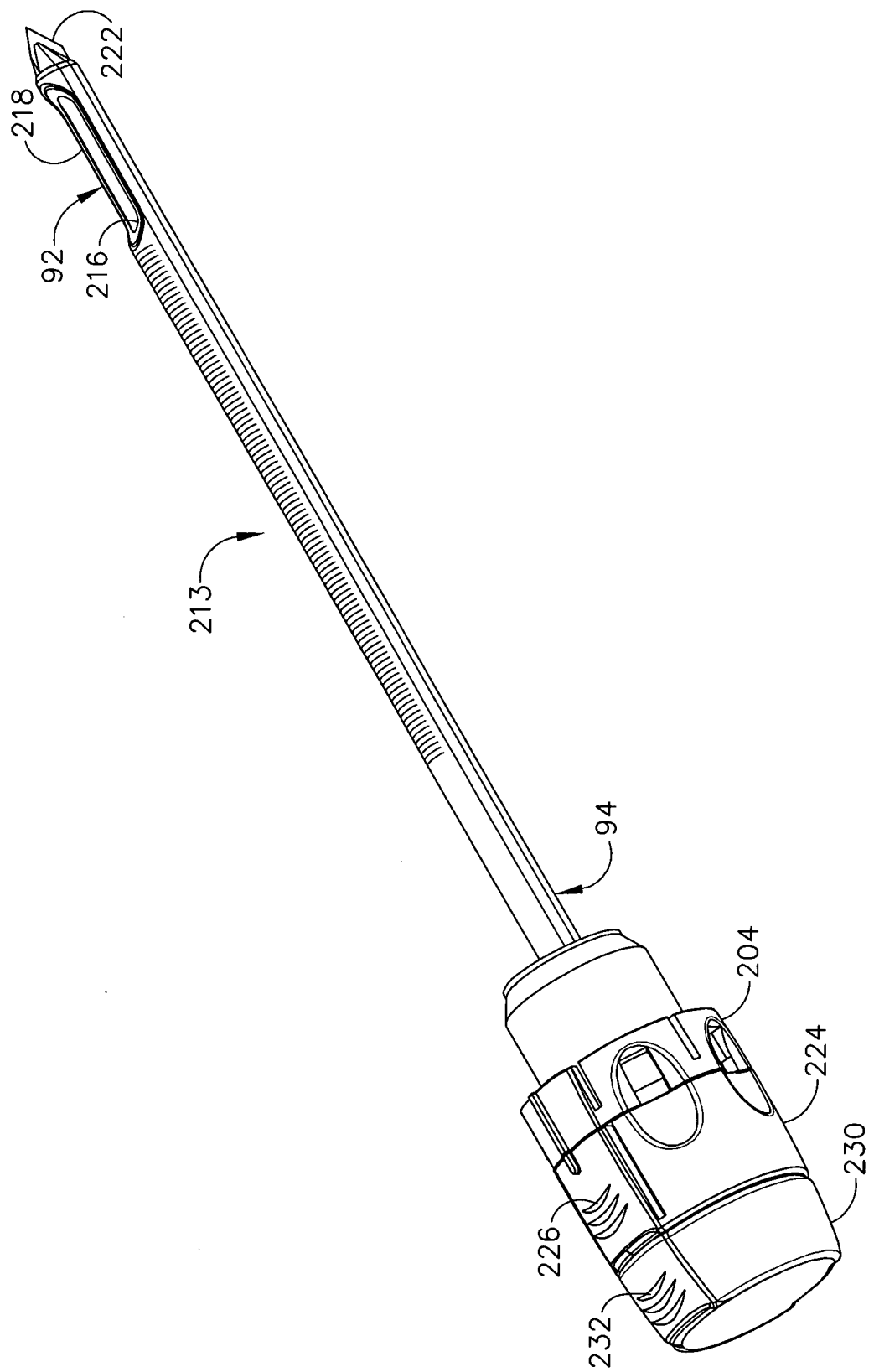
FIG. 7 is an isometric view of the trocar and sleeve of the biopsy system of FIG. 1.
Figure 8:
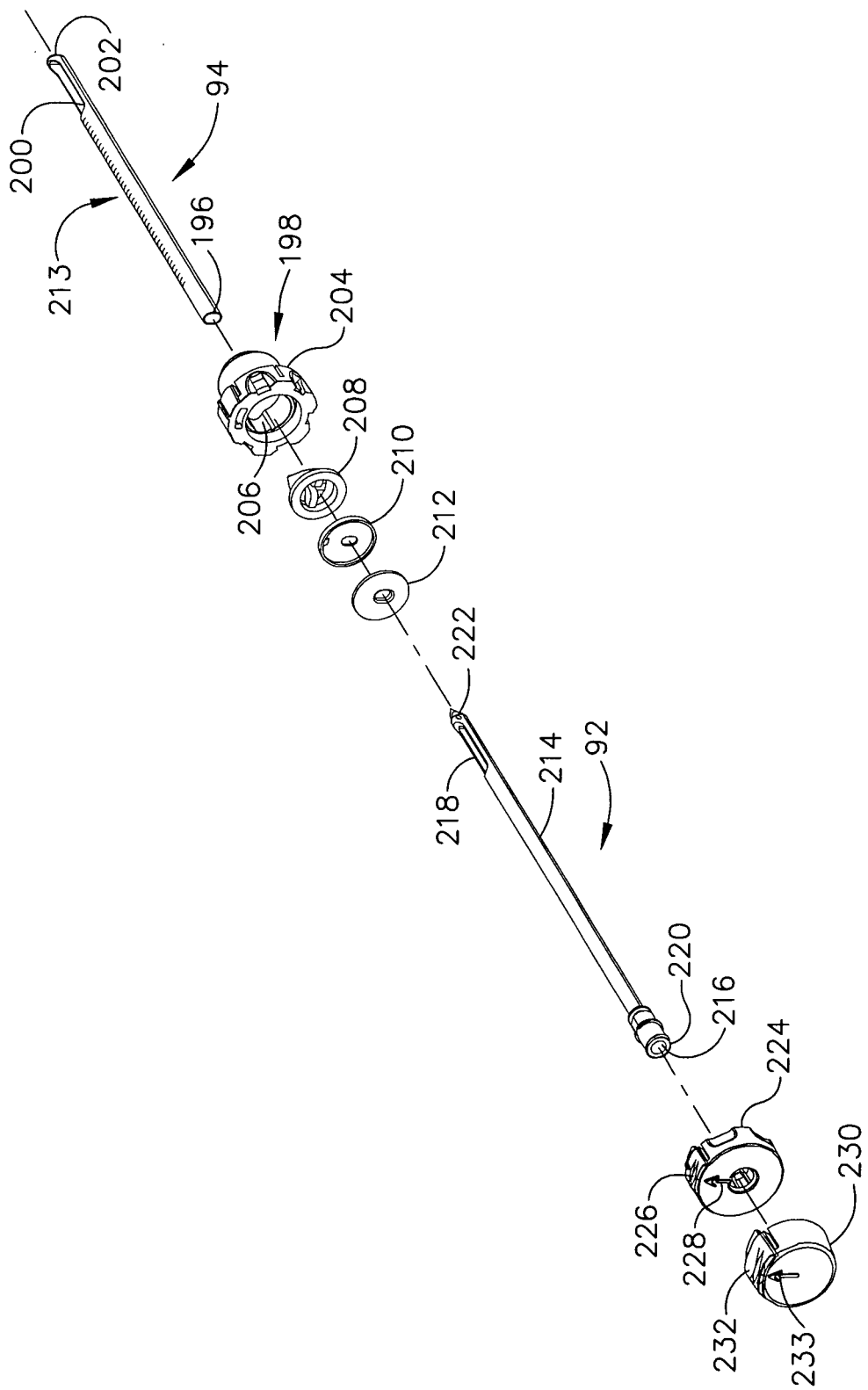
FIG. 8 is an isometric exploded view of the trocar and sleeve of FIG. 7.
Figure 9:
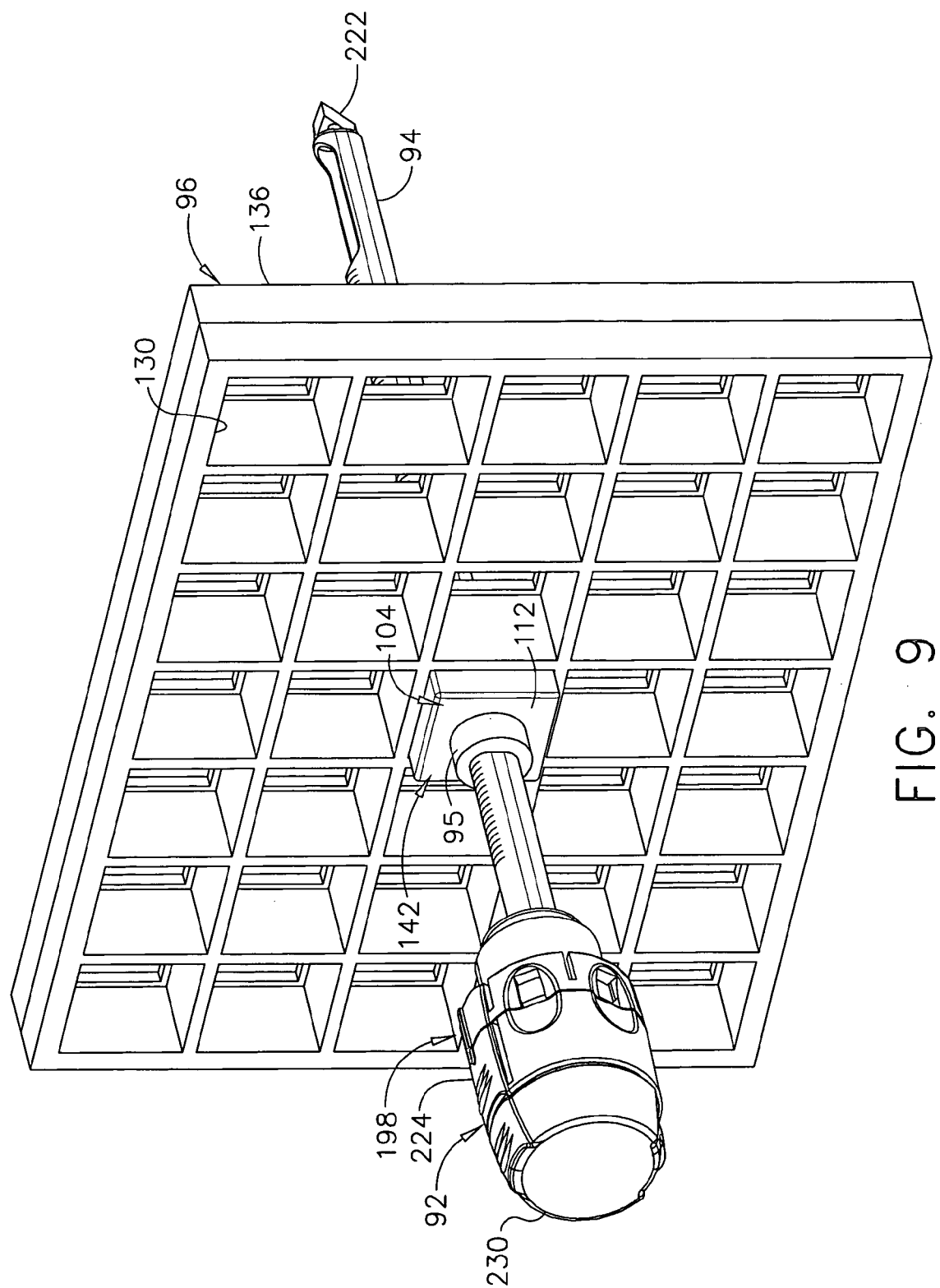
FIG. 9 is an isometric view of a trocar and sleeve of FIG. 7 with a depth stop deice of FIG. 1 inserted through the guide cube and grid plate of FIG. 6.

In FIGS. 7-9, in the illustrative version, the trocar 92 is slid into the sleeve 94 and the combination is guided through the guide cube 104 (FIG. 9) to the biopsy site within the breast tissue. The sleeve 94 includes a hollow shaft (or cannula) 196 that is proximally attached to a cylindrical hub 198 and has a lateral aperture 200 proximate to an open distal end 202. The cylindrical hub 198 has an exteriorly presented thumbwheel 204 for rotating the lateral aperture 200. The cylindrical hub 198 has an interior recess 206 that encompasses a duckbill seal 208, wiper seal 210 and a seal retainer 212 to provide a fluid seal when the shaft 196 is empty and for sealing to the inserted introducer (trocar) 92. Longitudinally spaces measurement indicia 213 along an outer surface of the hollow shaft 196 visually, and perhaps physically, provide a means to locate the depth stop device 95 of FIG. 1.

The trocar 92 advantageously incorporates a number of components with corresponding features. A hollow shaft 214 includes a fluid lumen 216 that communicates between an imagable side notch 218 and a proximal port 220. The hollow shaft 214 is longitudinally sized to extend, when fully engaged, a piercing tip 222 out of the distal end 202 of the sleeve 94. An obturator thumbwheel cap 224 encompasses the proximal port 220 and includes a locking feature 226, which includes a visible angle indicator 228 (FIG. 8), that engages the sleeve thumbwheel 204 to ensure that the imagable side notch 218 is registered to the lateral aperture 200 in the sleeve 94. An obturator seal cap 230 may be engaged proximally into the obturator thumbwheel cap 224 to close the fluid lumen 216. The obturator seal cap 230 includes a locking or locating feature 232 that includes a visible angle indicator 233 that corresponds with the visible angle indicator 228 on the obturator thumbwheel cap 224, which may be fashioned from either a rigid, soft, or elastomeric material. In FIG. 9, the guide cube 104 has guided the trocar 92 and sleeve 94 through the grid plate 96.

Figure 10:
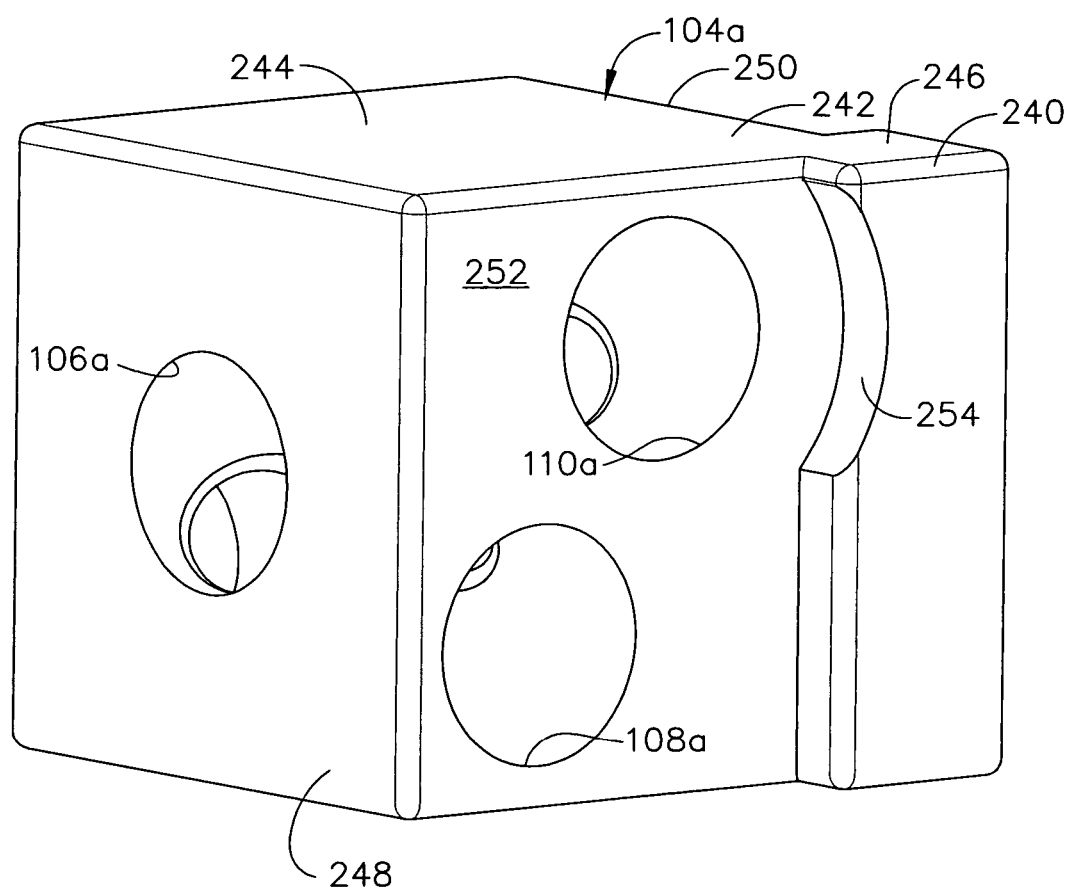
FIG. 10 is an alternative guide cube for the biopsy system of FIG. 1 with two-axes of rotation and self-grounding features.
Figure 11:
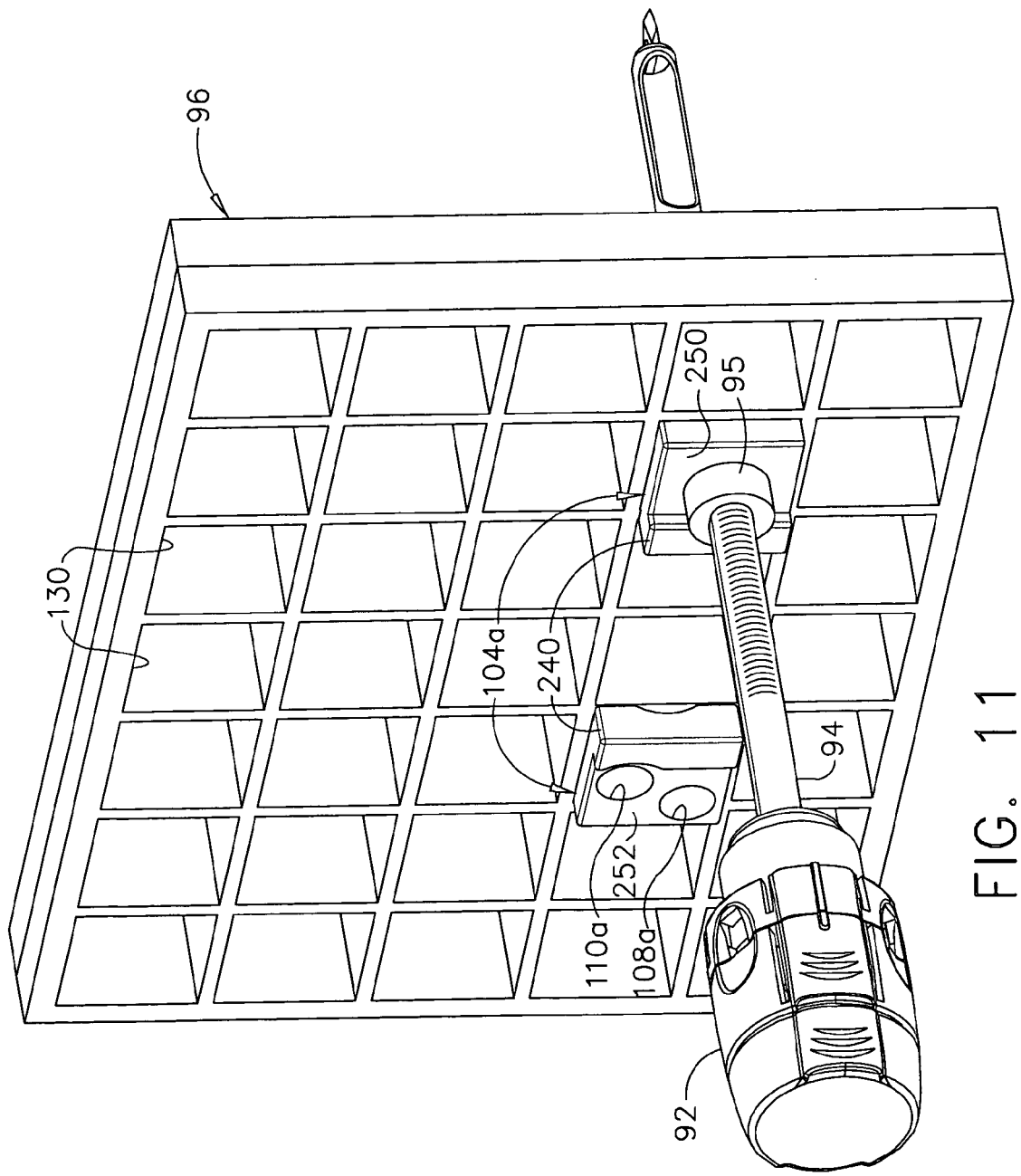
FIG. 11 is an isometric view of the trocar and sleeve of FIG. 7 inserted into one of two guide cubes of FIG. 10 inserted into the grid plate of FIG. 1.

In FIGS. 10-11, an alternative guide cube 104a has rotation in two axes but is self-grounding by means of an added rectangular prism 240 which has a shared edge with a cubic portion 242 of the guide cube 104a. When viewed orthogonally to the shared cube edge, a larger square face 244 of the cubic portion 242 overlaps with a smaller square face 246 of the rectangular prism 240 to correspond with the desired size of an exposed proximal portion 248 of the inserted guide cube 104a. The rectangular prism 240 allows proximal exposure of one of two adjacent faces 250, 252 of the guide cube 104a and then turning each to one of four quarter turn rotational positions. In the illustrative version, first face. 250 has a central guide hole 106a and the second face 252 has a corner guide hole 108a, and an off-center guide hole 110a. A radial recess 254 is relieved into the rectangular prism 240 to allow grounding of the depth stop device 95 against the face 252 when the off-center guide hole 110a is used.

Figure 12:
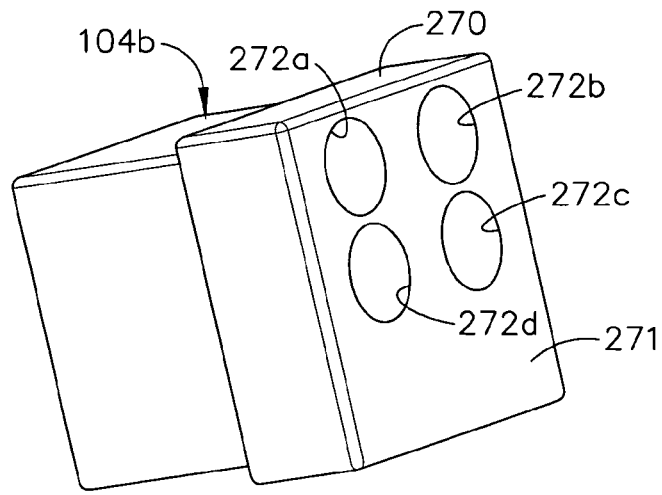
FIG. 12 is an aft isometric view of a further alternative guide cube with four angled, parallel guide holes for the biopsy system of FIG. 1.
Figure 13:
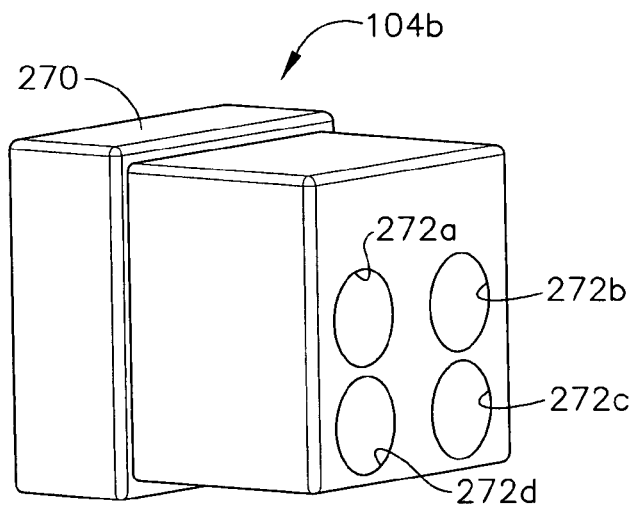
FIG. 13 is a front isometric view of the guide cube of FIG. 12.
Figure 14:
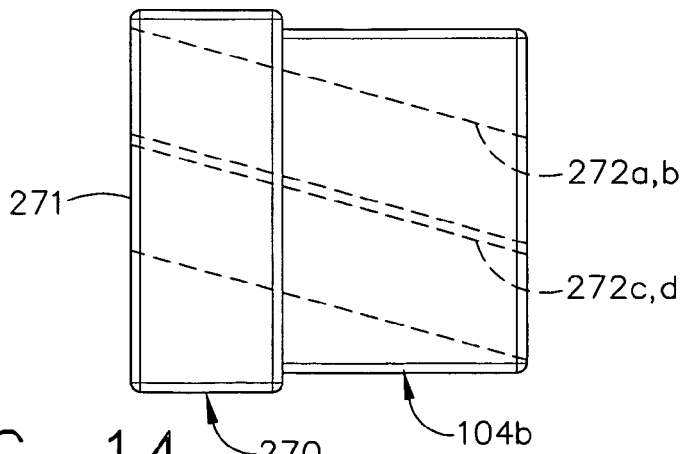
FIG. 14 is a right side view of the guide cube of FIG. 12 with the angled, parallel guide holes depicted in phantom.

In FIGS. 12-14, another alternative guide cube 104b has a proximal enlarged hat portion 270 about a proximal face 271 that grounds against the selected square recess 130 in the grid plate 96 (FIG. 6) and allows rotation about one axis to one of four quarter turn positions. Four angled guide holes 272a, 272b, 272c, 272d allow accessing not only an increased number of insertion points within the selected square recess 130 but also a desired angle of penetration rather than being constrained to a perpendicular insertion.

Figure 15:
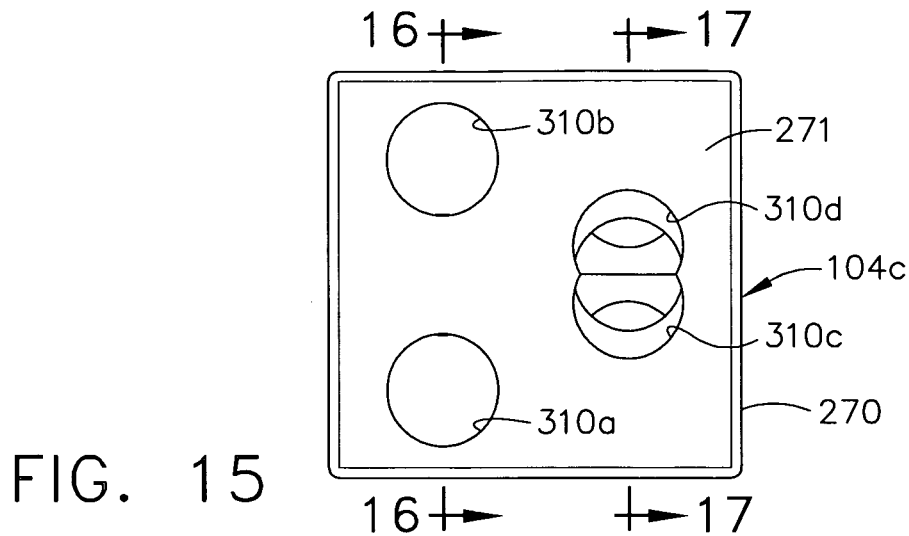
FIG. 15 is an aft view in elevation of yet another alternative guide cube for the biopsy system of FIG. 1 with a pair of converging guide holes and a pair of diverging guide holes.
Figure 16:
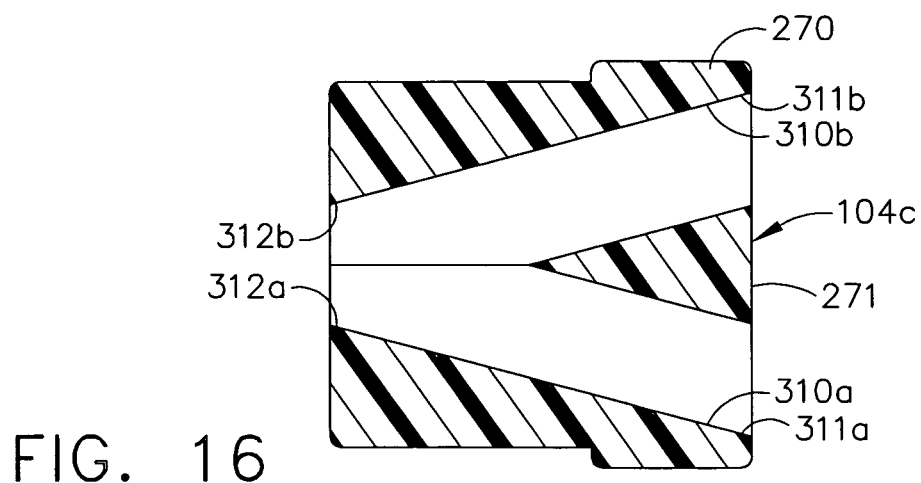
FIG. 16 is a left side view of the guide cube of FIG. 15 taken in cross section along lines 16-16 through the pair of converging guide holes.
Figure 17:
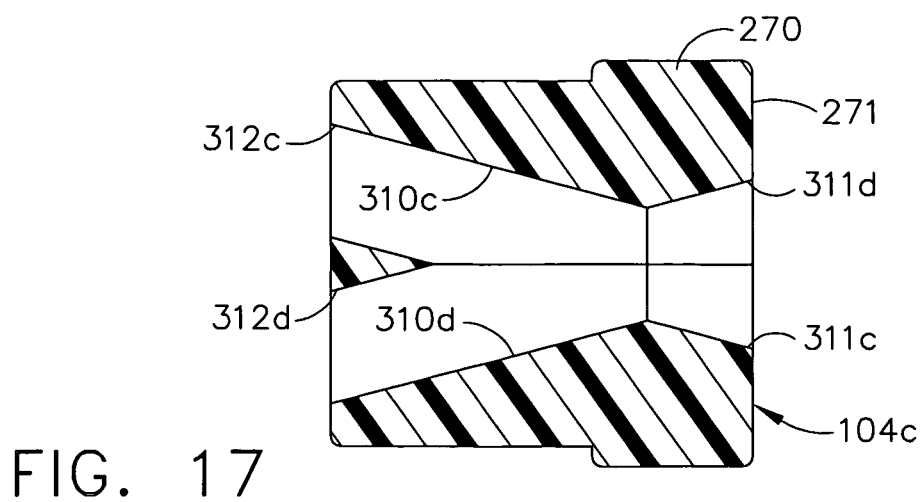
FIG. 17 is a left side view of the guide cube of FIG. 15 taken in cross section along lines 17-17 through the pair of diverging guide holes.

In FIGS. 15-17, an additional alternative guide cube 104c also has the proximal enlarged hat portion 270 about the proximal face 271 that grounds against the selected square recess 130 in the grid plate 96 (FIG. 6) and allows rotation about one axis to one of four quarter turn positions. The guide holes are depicted as a first pair of converging angled through holes 310a, 310b having outwardly spaced proximal openings 311a, 311b (FIG. 15), respectively, that communicate with partially intersecting distal openings 312a, 312b, respectively. The guide holes are also depicted as a second pair of diverging angled through holes 310c, 310d having partially intersecting proximal openings 311c, 311d, respectively, that communicate with outwardly spaced distal openings 312c, 312d.

Figure 18:
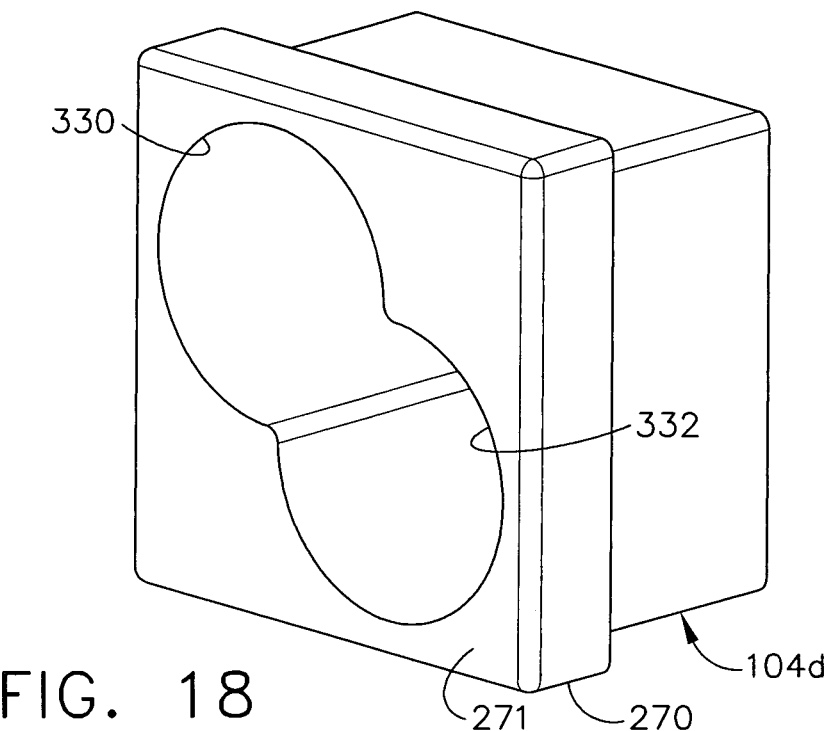
FIG. 18 is an isometric view of a two hole guide cube for the biopsy system of FIG. 1.
Figure 19:
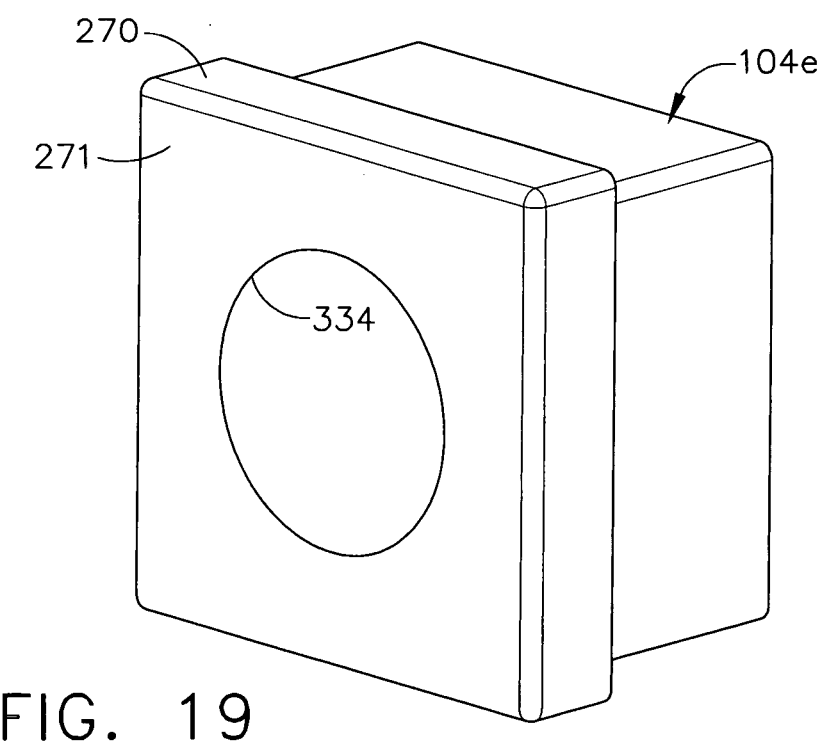
FIG. 19 is an isometric view of a one-hole guide cube for the biopsy system of FIG. 1.
Figure 20:
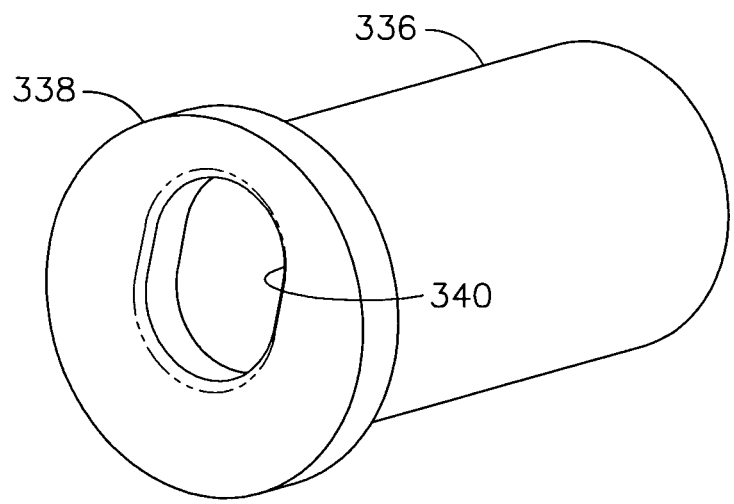
FIG. 20 is a rotating guide for guiding the trocar and sleeve of FIG. 7 into either of the two-hole guide cube of FIG. 18 or the one-hole guide cube of FIG. 19.
Figure 21:
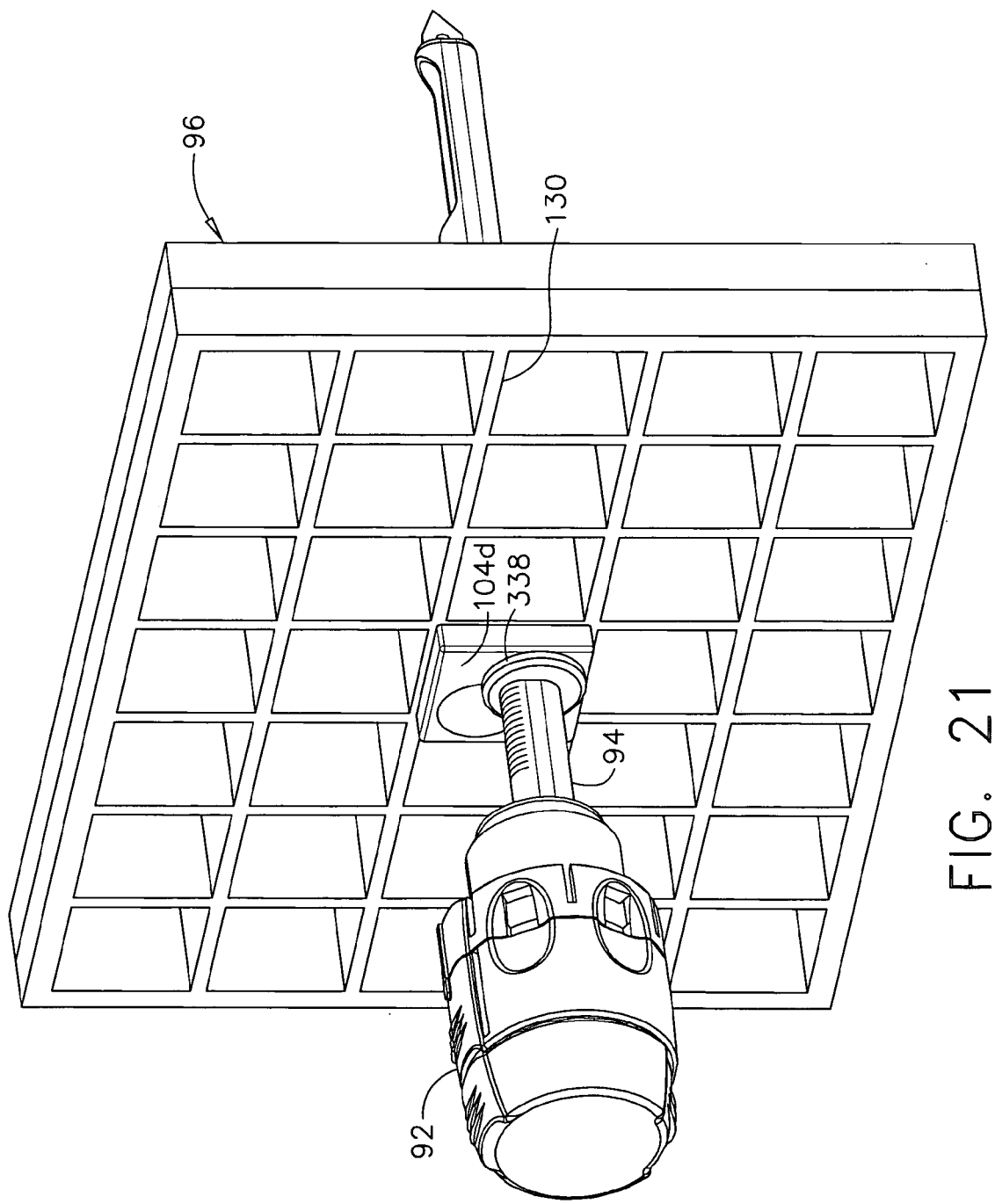
FIG. 21 is an aft isometric view of the trocar and sleeve of FIG. 7 inserted through the rotating guide of FIG. 20 into the two-hole guide cube of FIG. 18.

In FIG. 18, a further alternative two-hole guide cube 104d has two enlarged guide holes 330, 332 accessed through the proximal face 271 in the enlarged proximal hat portion 270. Similarly, in FIG. 19, a one hole guide cube 104e has one enlarged guide hole 334 accessed through the proximal face 271 in the enlarged proximal hat portion 270. Each guide cube 104d, 104e may receive a cylindrical rotating guide 336 (FIG. 20) with an integral, proximal depth ring stop 338. In FIGS. 20, 21, a through hole 340 in the cylindrical guide 336 is sized to receive a biopsy instrument cannula (e.g., probe 90, sleeve 94) by being oval in cross section in the illustrative version. It should be appreciated that the cylindrical guide 336 may provide structural support to the guided portion of the biopsy instrument support as well as facilitate axial rotation thereof, especially for a non cylindrical biopsy instrument cannula.

It should be appreciated that the two-hole and one-hole guide cubes 104d, 104e and rotating guide 336 may comprise a guide cube set, perhaps with additional guide cubes (not shown) having uniquely positioned guide holes. With the enlarged guide holes 330-340 to accommodate the rotating guide 336, too much overlap of guide holes (e.g., 330, 332) may result in insufficient support by the rotating guide 336 for the inserted biopsy instrument cannula. Thus, fine positioning is accomplished by selecting one of the available guide cubes 104d, 104e for the desired position within a selected grid aperture.

Figure 22:
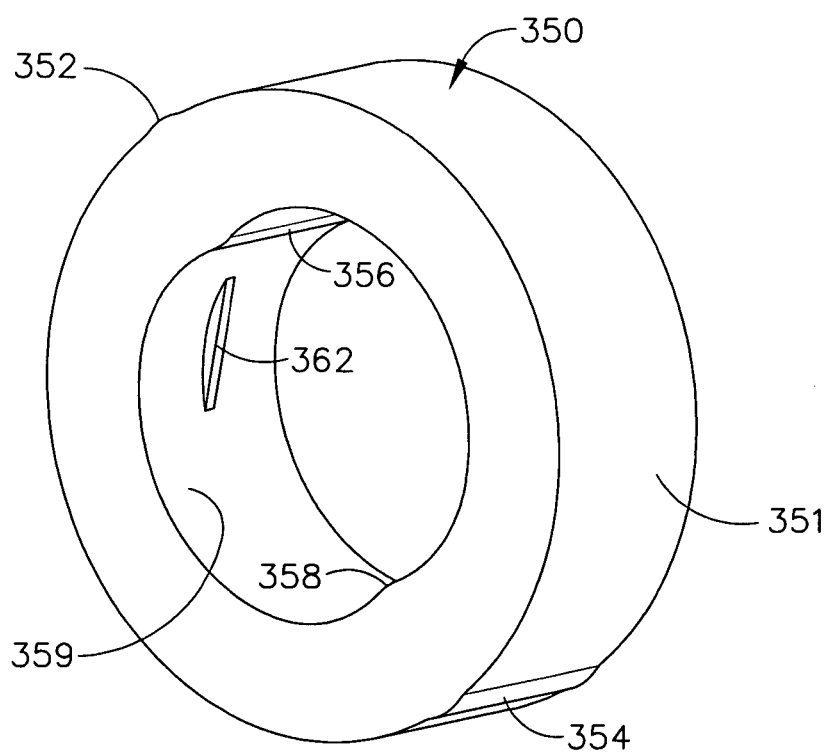
FIG. 22 is an isometric locking O-ring for the biopsy system of FIG. 1.
Figure 23:
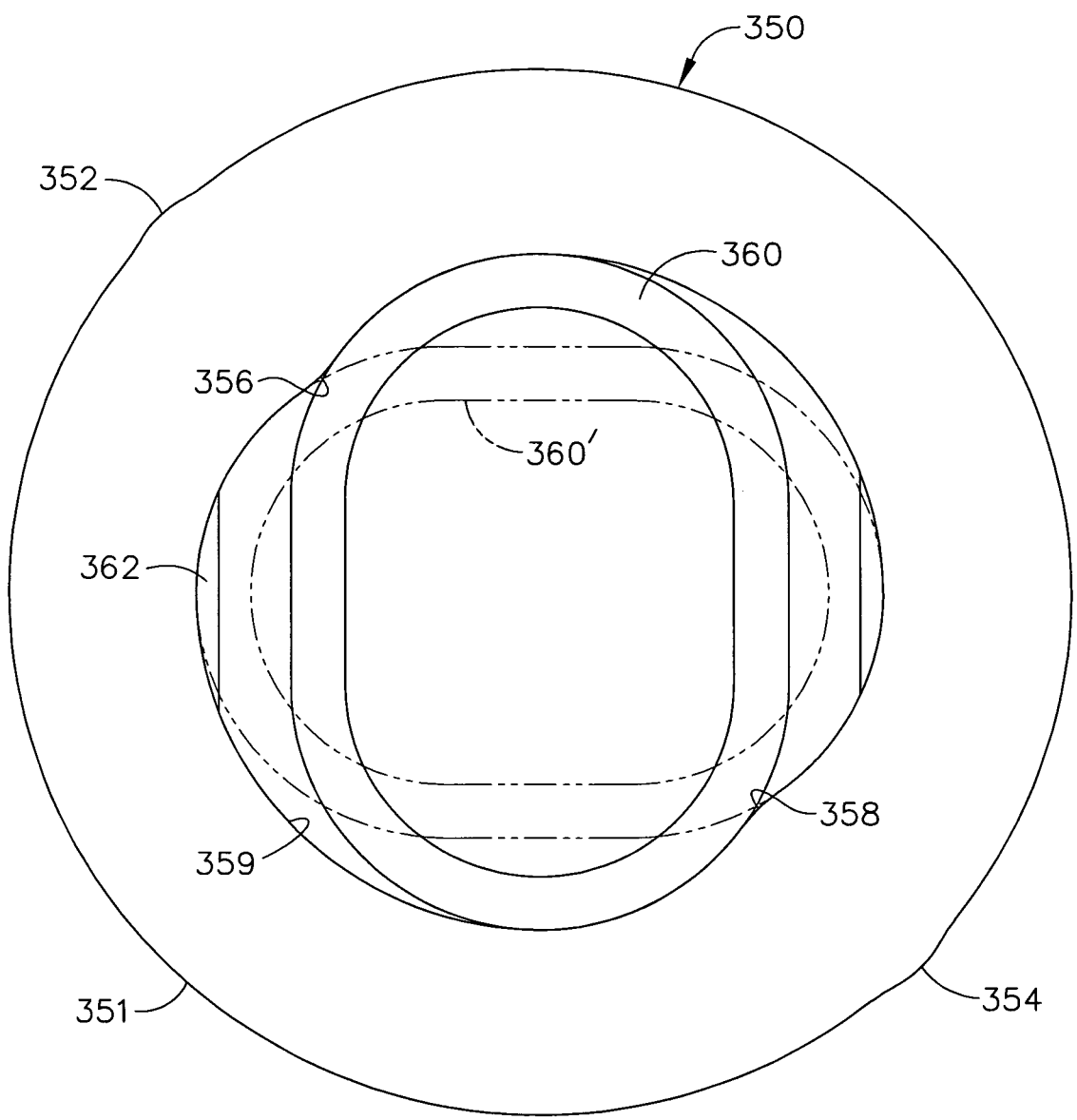
FIG. 23 is an aft view of the locking O-ring of FIG. 22 with a cross section of a biopsy instrument cannula shown in both an unlocked orientation and rotated a quarter turn into a locked orientation depicted in phanton.

In FIGS. 22, 23, a locking O-ring feature may be advantageously incorporated into a depth ring stop (rotating guide) 350. Having to rely upon constant frictional engagement of the depth ring stop (rotating guide) 350 alone would result in difficulty in installing the ring stop 350 to the desired position or being too readily displaced to serve as a stopping structure. In the exemplary version, an outer circumference surface 351 of the ring stop 350 includes left and right outer longitudinal ridges 352, 354 that aid in gripping and orienting the depth ring stop 350 while turning for locking and unlocking. As viewed from behind, opposing inner longitudinal ridges 356, 358 formed in a generally cylindrical inner diameter 359 abut respectively at an upper left and lower right side of an oval cannula 360 (FIG. 23) oriented with its elongate cross section vertically in an unlocked position. The inner longitudinal ridges 356, 358 allow a quarter turn clockwise of the oval cannula, depicted as 360', to a locked position deforming an inner tangential locking rib 362.

Figure 24:
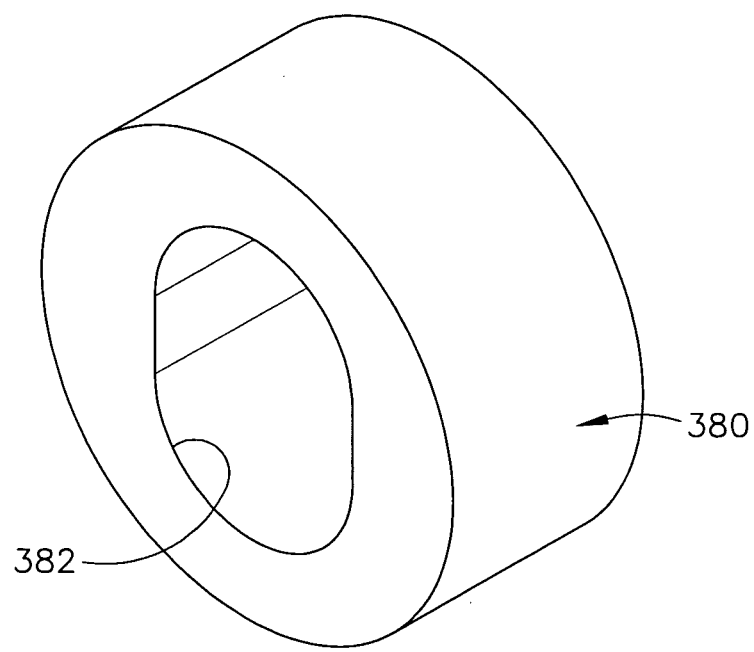
FIG. 24 is an isometric view of a cylindrical rotating guide formed of elastomeric material with an oval through hole for the biopsy system of FIG. 1.
Figure 25:
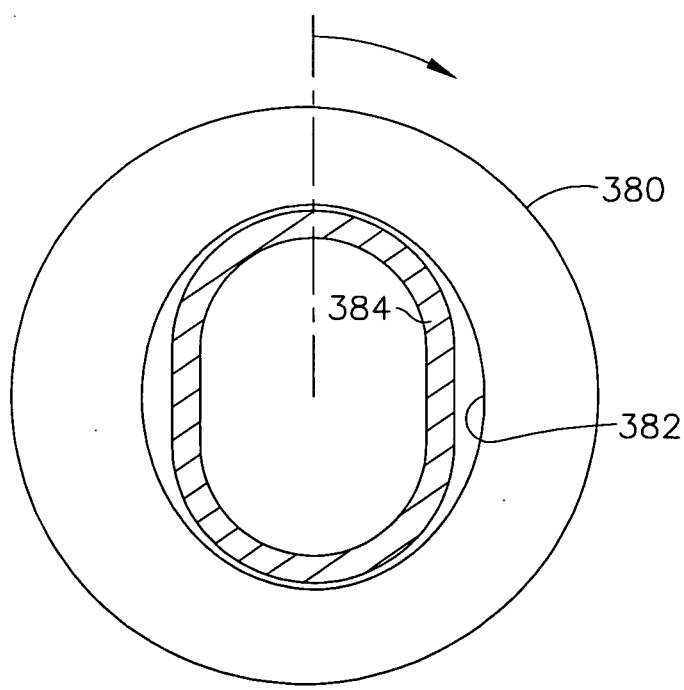
FIG. 25 is an aft view of the cylindrical rotating guide of FIG. 24 with a cross sectional view of an unlocked oval-shaped biopsy instrument cannula inserted in the oval through hole.
Figure 26:
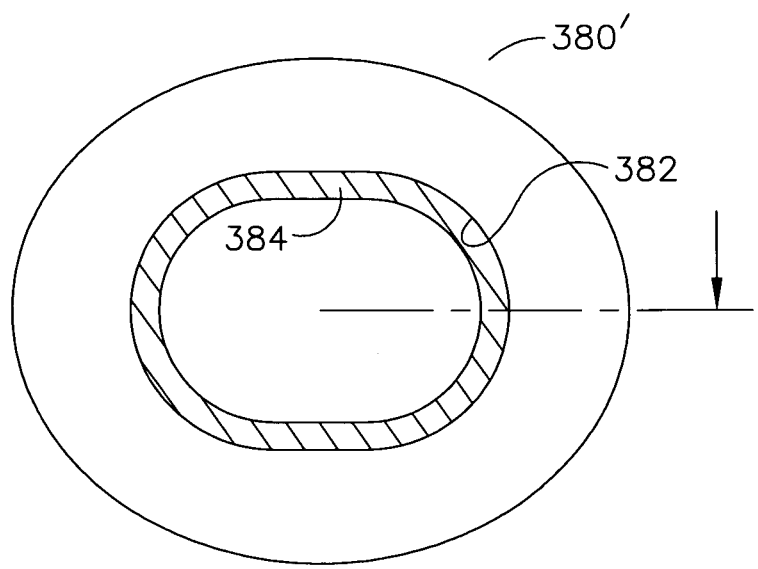
FIG. 26 is an aft view of the cylindrical rotating guide and biopsy instrument cannula of FIG. 25 with the cylindrical rotating guide rotated a quarter turn relative to the cannula to elastomerically lock thereon.

It should be appreciated that these orientations and geometry are illustrative. An amount of rotation to lock and unlock, for instance, may be less than or more than a quarter turn. In addition, noncircular features on an outer diameter of the depth ring stop 350 may be omitted. Other variations may be employed. For example, in FIGS. 24-25, a cylindrical rotating guide 380, formed of a resilient polymer has an elongate through hole 382 shaped to permit insertion of an oval biopsy cannula 384. In FIG. 26, turning the cylindrical rotating guide 380 a quarter turn in either direction to a locked position, depicted at 380', causes the cylindrical rotating guide 380' to deform, binding onto the biopsy instrument cannula 384, thereby serving as a depth stop.

Figure 27:
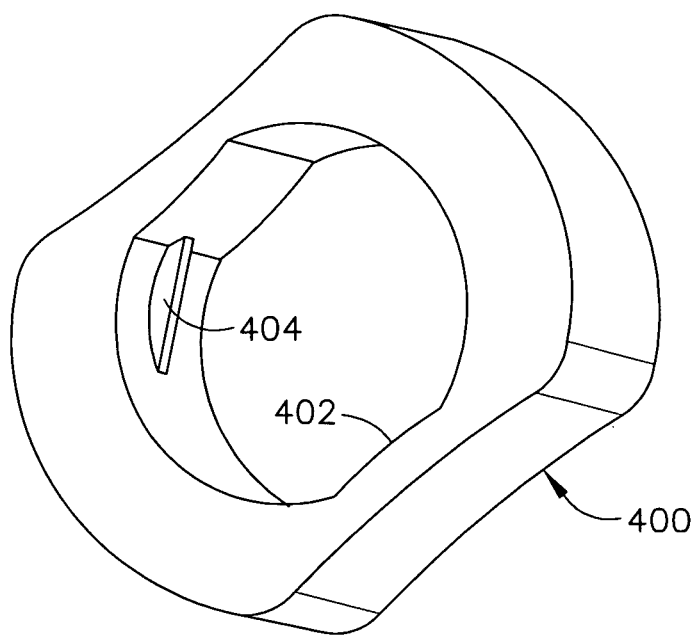
FIG. 27 is an isometric view of a flattened oval rotating guide for the biopsy system of FIG. 1.

Similarly, in FIG. 27, a rotating guide 400 is oval shaped with flattened elongate sides and with a corresponding elongate through hole 402. The outer shape may be tactile, advantageous for gripping as well as provide a visual indication of being locked or unlocked. A resilient tangential rib 404 crossing one inner corner of the elongate through hole 402 is positioned to bind against an inserted biopsy instrument cannula (not shown) when the rotating guide 400 is turned a quarter turn to a locking position.

Figure 28:
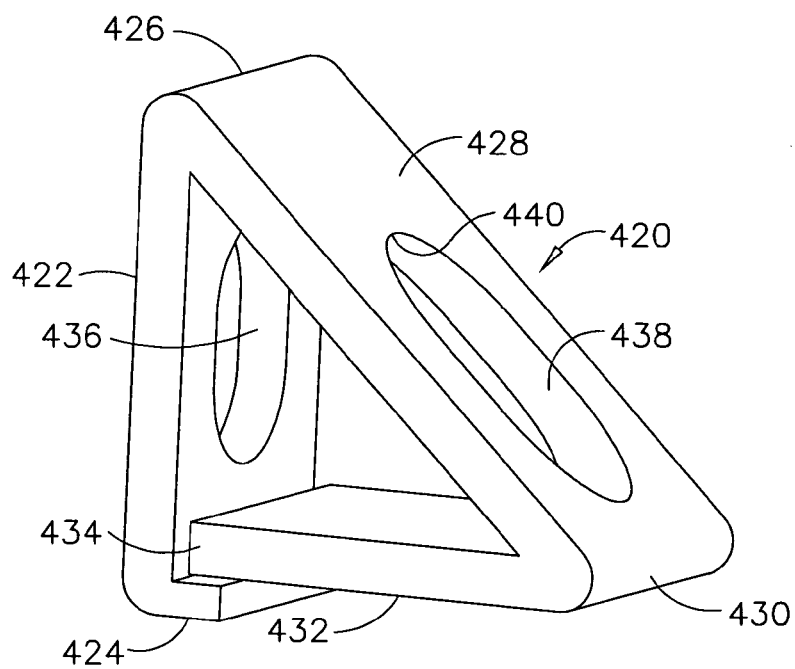
FIG. 28 is an isometric view of a triangular clip depth stop for the biopsy system of FIG. 1.

In FIG. 28, a triangular clip depth stop 420 has a transverse front surface 422 with a proximally turned lower lip 424 and an upper lateral edge 426 attached to a downwardly and proximally ramped member 428 whose lower lateral edge 430 bends distally to form a horizontal locking actuator member 432 whose distal edge 434 rests upon the lower lip 424. A front vertically elongate aperture 436 in the transverse front surface 422 is shaped to approximate the outer diameter of an inserted biopsy instrument cannula (not shown). An aft elongate aperture 438 formed in the downwardly and proximally ramped member 428 is a distal horizontal projection of the front vertically elongate aperture 436 when the locking actuator member 432 is upwardly raised, thus allowing insertion of the biopsy instrument cannula through both apertures 436, 438. Upon release of the locking actuator member 432, an upper inner surface 440 of the aft elongate aperture 438 lowers, binding upon the inserted biopsy instrument cannula, allowing the transverse front surface 422 to serve as a positive depth stop.

Figure 29:
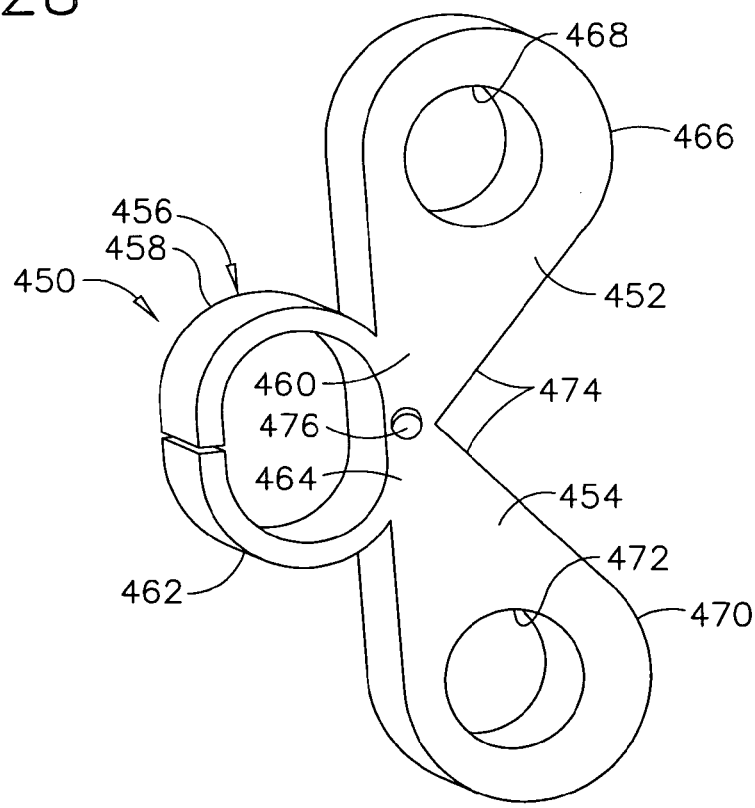
FIG. 29 is an isometric view of a scissor-like depth stop clip for the biopsy system of FIG. 1.

In FIG. 29, a scissor-like clip depth stop 450 is cut out of a layer of resilient material. In particular, an upper arm portion 452 and a lower arm portion 454 are attached to one radiating vertically away from each other toward the same lateral side (right as depicted) from a split cylindrical grasping portion 456 separated longitudinally on a lateral side opposite to the arm portions 452, 454 (left as depicted). In particular, an upper gripping half-cylindrical member 458 is attached at its right side to a lower portion 460 of the upper arm portion 452. A lower gripping half-cylindrical member 462 is attached at its right side to an upper portion 464 of the lower arm portion 454. An upper hemispheric portion 466 of the upper arm portion 452 includes an upper finger hole 468. A lower hemispheric portion 470 of the lower arm portion 454 includes a lower finger hole 472. A triangular recess 474 (opening rightward as depicted) formed by the arm portions 452, 454 and a longitudinal pin 476 inserted at the juncture between the arm portions 452, 454 predispose the arm portions 452, 454 to be resiliently drawn toward each other as the finger holes 468, 472 are gripped and moved together, thereby opening the upper and lower gripping half cylindrical members 458, 462, widening the separation of their left ends. In this unlocked position, a biopsy instrument cannula (not shown) may be inserted and positioned to a desired depth.

Figure 30:
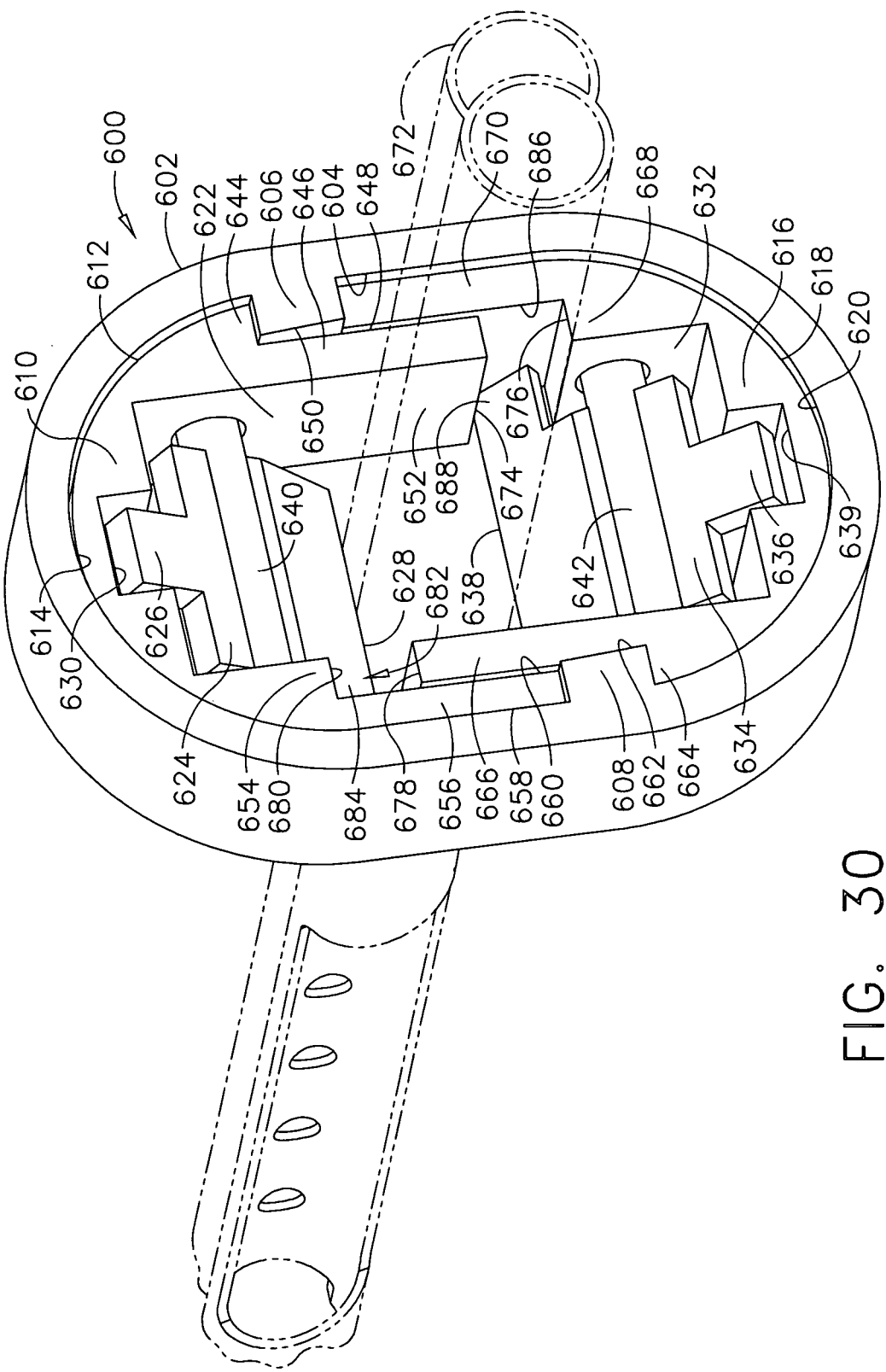
FIG. 30 is an aft isometric view of a shutter depth stop with inserted biopsy instrument cannula for the biopsy system of FIG. 1.

In FIG. 30-33 a shuttered depth stop 600 includes a resilient oval shell 602 with a corresponding oval aperture 604 with an upper right tab 606 projecting inwardly to the left and with a lower left tab 608 projecting inwardly to the right when viewed from behind (FIG. 30). An upper resilient member 610 has a generally horseshoe-shaped outer surface 612 that conforms to an upper portion 614 of the oval aperture 604. A lower resilient member 616 has a generally horseshoe-shaped outer surface 618 that conforms to a lower portion 620 of the oval aperture 604. In the illustrative version, the upper and lower resilient members 610, 616 are identical but are rotated a half turn about a longitudinal axis with respect to each other. Moreover, the entire shuttered depth stop 600 is symmetric about its vertical axis defined by its longest dimension or about a horizontal axis defined by its second longest dimension.

A downwardly open rectangular prismatic recess. 622 formed in the upper resilient member 610 is sized to receive an upper shutter 624 having an upper center tab 626 and a lower acute edge 628. A top center rectangular slot 630 formed in the upper resilient member 610 communicates with the downwardly open rectangular prismatic recess 622 and receives the upper center tab 626. An upwardly open rectangular prismatic recess 632 formed in the lower resilient member 616 is sized to receive a lower shutter 634 having a lower center tab 636 and an upper acute edge 638. A bottom center rectangular slot 639 formed in the lower resilient member 616 communicates with the upwardly open rectangular prismatic recess 632 and receives the lower center tab 636. An upper horizontal pin 640 attached horizontally as depicted across the upper shutter 624 is received for rotation onto opposite lateral sides of the downwardly open rectangular prismatic recess 622. A lower horizontal pin 642 attached horizontally as depicted across the lower shutter 634 is received for rotation onto opposite lateral sides of the upwardly open rectangular prismatic recess 632.

The right side of the upper resilient member 610 includes a right outward shoulder 644 that rests upon the upper right tab 606 of the resilient oval shell 602. A laterally recessed downward arm 646 is attached to the right shoulder 644 and extends downwardly with its outer surface 648 vertically aligned with an innermost edge 650 of the right outward shoulder 644 and with its inner surface 652 defining the downwardly open generally rectangular prismatic recess 622. The left side of the upper resilient member 610 includes a left inward shoulder 654 that is laterally aligned with and opposite of the upper right tab 606 of the resilient oval shell 602. An outer downward arm 656 is attached to the left inward shoulder 654 and extends downwardly with its outer surface 658 against oval aperture 604 and an innermost edge 660 vertically aligned with an inner surface 662 of the lower left tab 608 upon which the outer downward arm 656 rests.

Similarly, the lower resilient member 616 includes a left outward shoulder 664 attached to a laterally recessed upward arm 666 and a right inward shoulder 668 attached to an outer upward arm 670 that abuts an underside of the upper right tab 606. The laterally recessed downward arm 646 of the upper resilient member 610 extends downward past the longitudinal centerline of the shuttered depth stop 600 and an inserted biopsy instrument cannula 672. A lower edge 674 of the laterally recessed downward arm 646 is spaced away from an upper surface 676 of the right inward shoulder 668. In addition, an upper edge 678 of the laterally recessed upward arm 666 is spaced away from a lower surface 680 of the left inward shoulder 654. When the resilient oval shell 602 is relaxed as in FIGS. 30-32, this spacing between the left inward shoulder 654 and the upper edge 678 of the laterally recessed upward arm 666 defines an upper left rectangular recess 682 communicating rightward into the downwardly open rectangular prismatic recess 622 and sized to allow unimpeded swinging of a leftward extension 684 of the upper shutter 624. Spacing between the upper surface 676 of the right inward shoulder 668 and the lower edge 674 of the laterally recessed downward arm 646 defines a lower right rectangular recess 686 which communicates leftward into the upwardly open rectangular prismatic recess 632 which is sized to allow unimpeded swinging of a rightward extension 688 of the lower shutter 634.

Figure 31:
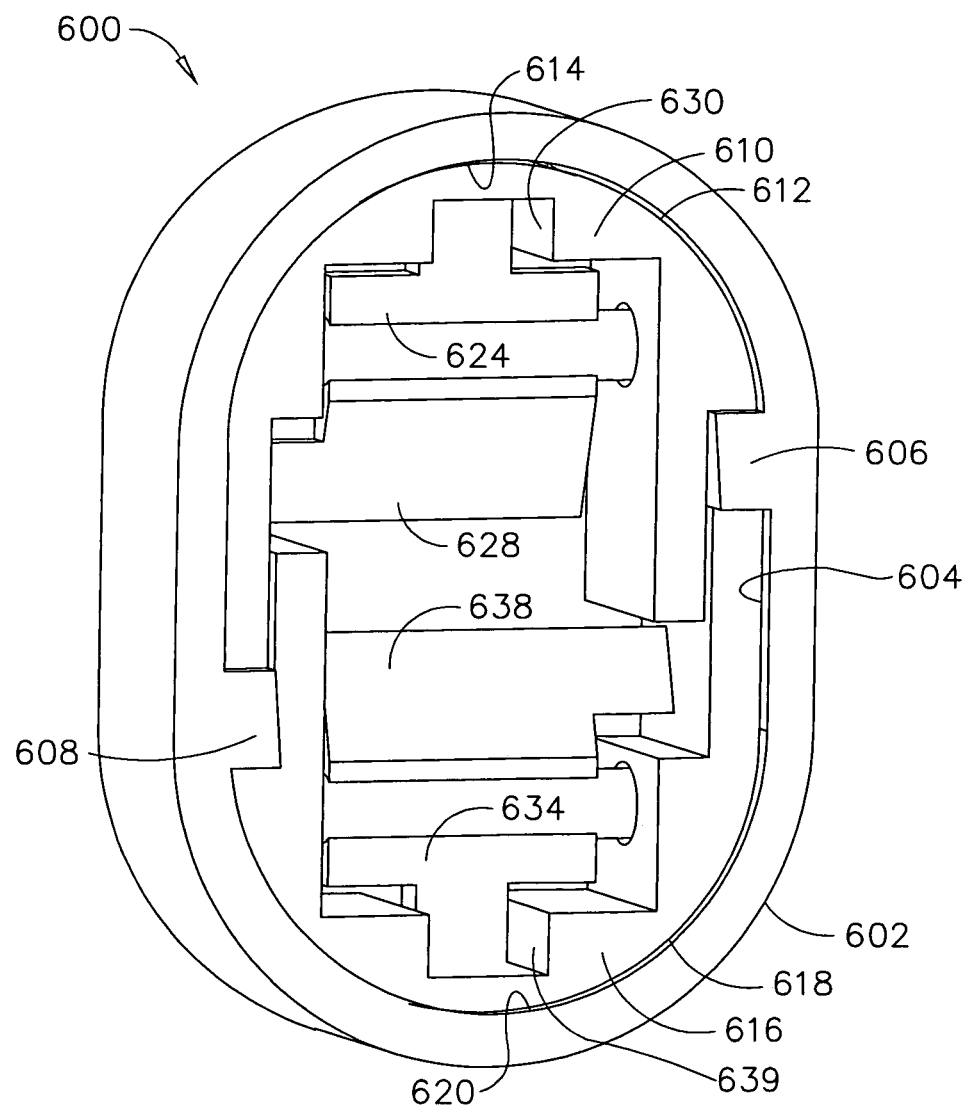
FIG. 31 is an aft view of the shutter depth stop of FIG. 30 prior to use.
Figure 32:
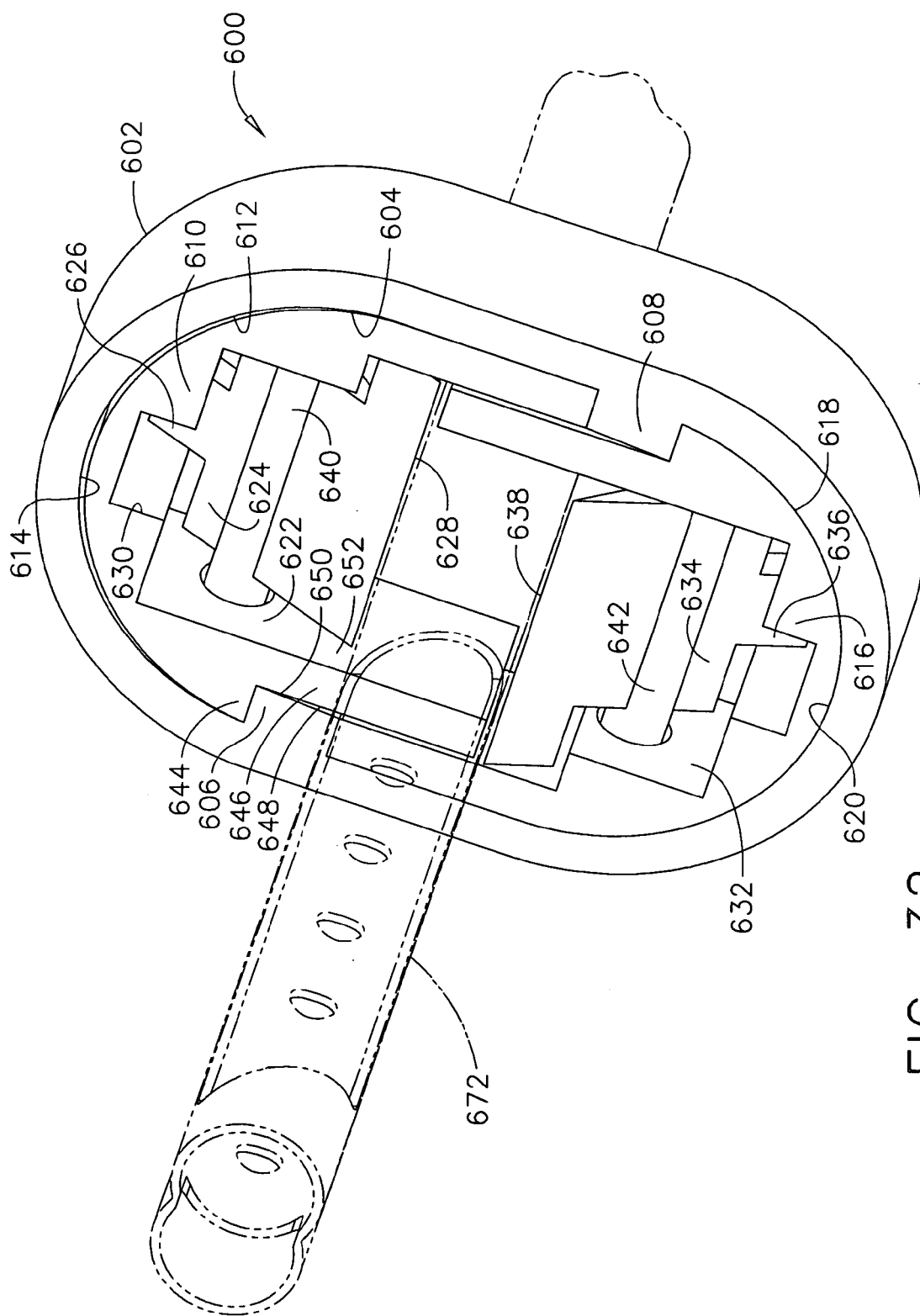
FIG. 32 is a front isometric view of the shutter depth stop and inserted biopsy instrument cannula of FIG. 30.
Figure 33:
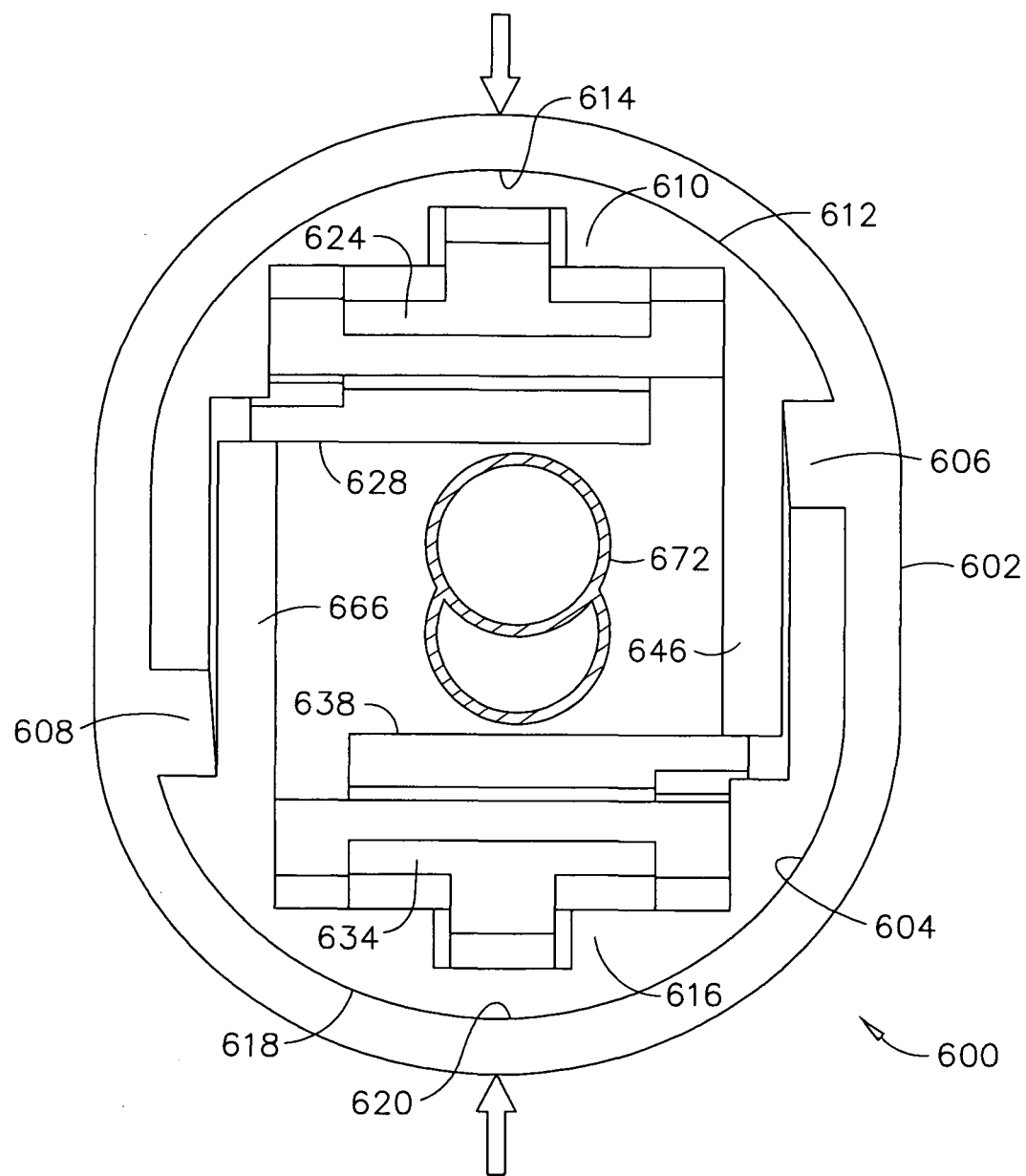
FIG. 33 is an aft view of the shutter depth stop and biopsy instrument cannula of FIG. 30 with the shutter depth stop vertically compressed into an unlocked state.

In FIG. 31, the shuttered depth stop 600 initially has closed upper and lower shutters 624, 634 due to restoring pressure from the top center rectangular slot 630 on the upper center tab 626 and from the bottom center rectangular slot 639 on the lower center tab 636 respectively. Insertion of a biopsy instrument cannula 672 from a selected side (thus the aft side) causes the upper and lower acute edges 628, 638 of the shutters 624, 634 to swing distally and outwardly but remain in contact due to the restoring pressure previously mentioned. Proximal retraction of the biopsy instrument cannula 672 frictionally rotates the acute edges 628, 638 proximally, and thus inwardly, binding upon the biopsy instrument cannula 672 preventing inadvertent retraction to serve as a depth stop. When retraction is desired, squeezing the resilient oval shell 602 to reduce the vertical height of the shutter depth stop 600 in FIG. 33 causes the laterally recessed downward arm 646 to open the lower shutter 634 and the laterally recessed upward arm 666 to open the upper shutter 624.

Alternatively, it should be appreciated that a single shutter may be employed in a shuttered depth stop consistent with aspects of the invention. As a further alternative or as an additional feature, grooves in the biopsy cannula may enhance engagement of one or two shutters to further avoid inadvertent proximal retraction of the positioned shuttered depth stop. Moreover, the grooves on the biopsy cannula may be ramped such that engagement is more prevalent against proximal retraction as compared to distal positioning. Further, such grooves may be along only a portion of the circumference of the biopsy cannula such that rotation of the shuttered depth stop also further unlocks from the biopsy cannula for positioning.

It should be appreciated that straight upper and lower acute edges 628, 638 of the two shutters 624, 634 may instead be contoured to closely approximate the transverse cross section of the encompassed shuttered depth stop 600 to increase the locking against inadvertent retraction.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, other imaging modalities may benefit from aspects of the present invention.

It should be appreciated that a grid plate 96 with a backing lip 140 may be used such that a guide cube rotatable to each of the six faces with four quarter turn positions for each face may achieve a large number of possible insertion positions and angles of insertion.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

It should be appreciated that various directional terms such as horizontal, vertical, left right, downward, upward, etc. have been used in conjunction with the orientation of depictions in the drawings. Applications consistent with the present invention may include usage of like components in other orientations.

It should be appreciated that biasing of the locking/unlocking components of various versions of a depth stop for a biopsy cannula described herein are advantageously formed out of an elastomeric material for economical manufacture. However, an assembly of rigid components biased by springs for biasing and/or actuating controls to move the locking surface out of engagement may be substituted to achieve similar results consistent with aspects of the present invention.

For example, the positioning and height of a central web of a breast coil may enable use of a medial grid plate used with a rotatable cube and penetrate from the medial side of the breast. For another example, a grid having a different geometric shape, such as hexagonal, may be employed.

As another example, each grid aperture of equilateral polygonal lateral cross section in a grid plate taper toward their distal opening to ground a similarly tapered guide block.

What is claimed:

1. An apparatus for guiding a biopsy instrument with respect to a breast compressive surface having a plurality of grid apertures, the apparatus being insertable at different orientations into one or more grid apertures selected from the plurality of grid apertures, the apparatus comprising:
   a guide device comprising a body sized and shaped to be received in one or more of the grid apertures, wherein the body comprises:
      a first pair of opposed faces, with at least one guide hole extending between the first pair of opposed faces, wherein a first axis passes through both faces of the first pair of opposed faces, and
      a second pair of opposed faces, with at least one guide hole extending between the second pair of opposed faces, wherein a second axis passes through both faces of the second pair of opposed faces, wherein the second axis is non-parallel relative to the first axis,
      wherein the body is insertable into a first grid aperture of the grid apertures along an axis of insertion that is parallel to the first axis,
      wherein the body is insertable into the first grid aperture along an axis of insertion that is parallel to the second axis.

2. The apparatus of claim 1, wherein the grid apertures comprise square apertures having a depth less than a lateral height and width of each square.

3. The apparatus of claim 1, further comprising a grounding structure attached to a selected one of the guide device and the breast compressive surface blocking distal movement of the guide device out of the grid apertures of the breast compressive surface.

4. The apparatus of claim 3, wherein the grounding structure comprises a lateral lip along a distal opening of each grid aperture in the grid plate.

5. The apparatus of claim 3, wherein the grounding structure comprises an enlarged proximal portion extending from the guide device.

6. The apparatus of claim 1, further comprising a pair of compressive surfaces movably attached to a patient support surface on opposing sides to locate the patient's breast, a selected one of the pair of compressive surfaces further comprises a grid plate comprising a plurality of grid apertures accessible from an aft side and at least substantially open from a front side presented to the breast.

7. The apparatus of claim 6, wherein the grid plate comprises a lateral fence and the other compressive surface comprises a medial fence.

8. The apparatus of claim 1, wherein the at least one guide hole extending between a selected one of the first pair of opposed faces and the second pair of opposed faces comprises a through hole aligned nonorthogonally between the selected one of the first pair of opposed faces and the second pair of opposed faces.

9. An apparatus for guiding a biopsy instrument into a breast of a patient supported upon a patient support surface, the apparatus comprising:
 a pair of compressive surfaces movably attached to the patient support surface on opposing sides to locate the patient's breast; a selected one of the pair of compressive surfaces further comprising a grid plate comprising a plurality of grid apertures accessible from an aft side and at least substantially open from a front side presented to the breast; and
 a guide device shaped for insertion into a selected one of the grid apertures and having at least first and second pairs of opposing faces, wherein said guide device comprises at least two sets of converging angled through holes, wherein each set of converging angled through holes extends between different pairs of the first and second pairs of opposing faces and are sized to receive a biopsy instrument cannula,
 wherein a first axis passes through the opposing faces of the first pair of opposing faces,
 wherein a second axis passes through the opposing faces of the second pair of opposing faces, wherein the second axis is perpendicular to the first axis,
 wherein the guide device is insertable into a selected one of the grid apertures along an axis of insertion that is parallel to the first axis,
 wherein the guide device is insertable into a selected one of the grid apertures along an axis of insertion that is parallel to the second axis.

10. A guide device for use in guiding a biopsy instrument with respect to a compression member having a plurality of grid apertures extending therethrough, the guide device comprising:
 a body configured to be received in one or more of the grid apertures, the body having multiple guide holes extending therethrough, wherein the body comprises a first face and a second face, wherein the first face and the second face are non-opposing, wherein a first axis passes through the first face, wherein a second axis passes through the second face;
 wherein the body is rotatable about a selected one of the first axis or a third axis to insert the body in a grid aperture of the plurality of grid apertures along an axis of insertion that is parallel to the first axis, to thereby position a first guide hole in the first face for guiding a biopsy instrument through the compression member; and
 wherein the body is rotatable about a selected one of the second axis or the third axis to insert the body in a grid aperture of the plurality of grid apertures along an axis of insertion that is parallel to the second axis, to thereby position a second guide hole in the second face for guiding the biopsy instrument through the compression member.

11. The guide device of claim 10, wherein the second axis for rotating the body is generally perpendicular to the first axis for rotating the body.

12. The guide device of claim 10, wherein the body further comprises at least two pair of opposed faces, each pair of opposed faces having one or more guide holes extending therethrough.

13. The guide device of claim 12 wherein the body comprises a cube-like structure.

14. The guide device of claim 12, wherein the one or more guide holes extending between the at least two pair of opposed faces are non-intersecting.

\* \* \* \* \*

UNITED STATES PATENT AND TRADEMARK OFFICE
CERTIFICATE OF CORRECTION

PATENT NO. : 8,568,333 B2
APPLICATION NO. : 11/415467
DATED : October 29, 2013
INVENTOR(S) : Hibner et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1555 days.

Signed and Sealed this
Twenty-first Day of April, 2015

Michelle K. Lee
*Director of the United States Patent and Trademark Office*